(12) United States Patent
Simpson et al.

(10) Patent No.: US 8,119,378 B2
(45) Date of Patent: *Feb. 21, 2012

(54) MICROBIAL ALCOHOL PRODUCTION PROCESS

(75) Inventors: Sean Dennis Simpson, Auckland (NZ); Christophe Collet, Auckland (NZ); Phuong Loan Tran, Auckland (NZ); Bakir Al-Sinawi, Auckland (NZ); Richard Llewellyn Sydney Forster, Auckland (NZ); Matthew James Rowe, Auckland (NZ); Gary Chan, Auckland (NZ); Kelly Marie Mahar, Auckland (NZ); Jennifer Mon Yee Fung, Auckland (NZ)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 12/921,584

(22) PCT Filed: Feb. 18, 2009

(86) PCT No.: PCT/NZ2009/000023
§ 371 (c)(1),
(2), (4) Date: Nov. 23, 2010

(87) PCT Pub. No.: WO2007/113878
PCT Pub. Date: Sep. 17, 2009

(65) Prior Publication Data
US 2011/0059499 A1    Mar. 10, 2011

Related U.S. Application Data

(60) Provisional application No. 61/036,061, filed on Mar. 12, 2008, provisional application No. 61/084,257, filed on Jul. 28, 2008.

(51) Int. Cl.
| | |
|---|---|
| C12P 7/06 | (2006.01) |
| C12P 7/00 | (2006.01) |
| C12N 1/20 | (2006.01) |
| C12P 1/00 | (2006.01) |
| C12P 1/04 | (2006.01) |
| C12P 7/16 | (2006.01) |
| C12P 7/52 | (2006.01) |
| C12P 7/54 | (2006.01) |
| C12M 1/36 | (2006.01) |

(52) U.S. Cl. ........ 435/161; 435/132; 435/140; 435/141; 435/160; 435/170; 435/41; 435/155; 435/286.1; 435/252.7

(58) Field of Classification Search .............. None
See application file for complete search history.

(56) References Cited

U.S. PATENT DOCUMENTS

| | | | |
|---|---|---|---|
| 4,539,293 | A | 9/1985 | Bergstrom et al. |
| 4,560,658 | A | 12/1985 | Datta et al. |
| 4,851,344 | A | 7/1989 | Simon et al. |
| 5,173,429 | A | 12/1992 | Gaddy et al. |
| 5,593,886 | A | 1/1997 | Gaddy |
| 5,753,474 | A | 5/1998 | Ramey |
| 5,807,722 | A | 9/1998 | Gaddy |
| 5,821,111 | A | 10/1998 | Grady et al. |
| 6,136,577 | A | 10/2000 | Gaddy |
| 6,340,581 | B1 | 1/2002 | Gaddy |
| 6,368,819 | B1 | 4/2002 | Gaddy et al. |
| 6,753,170 | B2 | 6/2004 | Gaddy et al. |
| RE39,175 | E | 7/2006 | Gaddy et al. |
| 7,196,218 | B2 | 3/2007 | Gaddy et al. |
| 7,285,402 | B2 | 10/2007 | Gaddy et al. |
| 2003/0211585 | A1 | 11/2003 | Gaddy et al. |
| 2007/0275447 | A1 | 11/2007 | Lewis et al. |
| 2009/0203100 | A1 * | 8/2009 | Simpson et al. ............ 435/161 |
| 2009/0275787 | A1 * | 11/2009 | Forster et al. ............. 568/903 |
| 2010/0105115 | A1 * | 4/2010 | Simpson et al. ............ 435/135 |
| 2010/0317074 | A1 * | 12/2010 | Simpson et al. ............ 435/140 |
| 2010/0323417 | A1 * | 12/2010 | Simpson et al. ............ 435/157 |

FOREIGN PATENT DOCUMENTS

| | | |
|---|---|---|
| BR | 8700345 A | 12/1987 |
| JP | 62-011097 | 1/1987 |
| JP | 62-289189 | 12/1987 |
| WO | WO 2007/117157 | 10/2007 |
| WO | 2008/028055 | 3/2008 |
| WO | WO 2008/115080 | 9/2008 |
| WO | 2008/154301 | 12/2008 |
| WO | 2009/020747 | 2/2009 |
| WO | WO 2009/022925 | 2/2009 |

OTHER PUBLICATIONS

DSMZ "Microorganisms: *Clostridium*" German Collection of Microorganisms and Cell Cultures (DSMZ) <http://www.dsmz.de/microorganisms/html/bacteria.genus/clostridium.html> and <http://www.dsmz.de/microorganisms/html/strains/strain.dsm010061.html>, 2004, accessed online Aug. 24, 2011, 19 pages.*

Kopke,M; Mihalcea,C; Bromley,JC; Simpson,SD "Fermentative production of ethanol from carbon monoxide" Current Opinion in Biotechnology, 2011, 22(3), pp. 320-325.*

Najafpour, Ghasem et al. "Ethanol and acetate synthesis from waste gas using batch culture of *Clostridium ijungdahlii,*." Enzyme and Microbial Technology, 2006, vol. 38(1-2) pp. 223-228.

Huber et al. "Pterin cofactor, substrate specificity, and observations on the kinetics of the reversible tungsten-containing aldehyde oxidoreductase from *Clostridium thermoaceticum.*" Arch Microbiol (1995) 164:110-118.

(Continued)

*Primary Examiner* — Chris R Tate
*Assistant Examiner* — Aaron J Kosar
(74) *Attorney, Agent, or Firm* — Frank S Molinaro

(57) ABSTRACT

The invention relates to the production of alcohols by microbial fermentation, particularly to production of alcohols by microbial fermentation of substrates comprising CO. It more particularly relates to processes for the production of alcohols from their corresponding acids in the presence of a substrate comprising CO. In particular embodiments, a fermentation reaction producing acid(s) and optionally alcohol(s) is perturbed such that at least a portion one or more of acid(s) is converted to alcohol.

18 Claims, 3 Drawing Sheets

OTHER PUBLICATIONS

Figure 1:
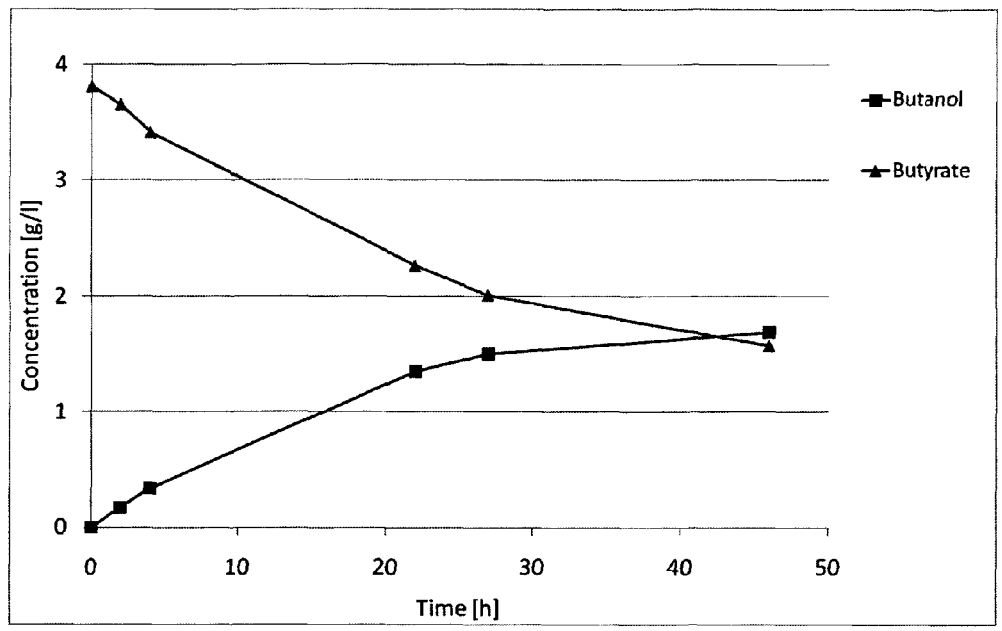

White et al. "The role of tungstate and/or molybdate in the formation of aldehyde oxidoreductase in *Clostridium thermoaceticum* and other acetogens; immunological distances of such enzymes." Arch Microbiol (1992) 158, 81-84.

Heyndrickx, et al. "The fermentation of glycerol of *Clostridium butyricum* LMG 1212 $t_2$ and 1213$t_1$, and *C. pasteurianum* LMG 3285." Applied Microbiology and Biotechnology. (1991) 34:637-642.

Phillips et al. "Synthesis Gas as Substrate for the Biological Production of Fuels and Chemicals." Applied biochemistry and biotechnology, 45(1), 145-157, 1994.

Abrini, et al. "*Clostridium autoethanogenum*, sp. Nov., an anaerobic bacterium that produces ethanol from carbon monoxide." Archives of Microbiology, 161(4), 345-351, 1994.

Ragsdale, Stephen W. "Life with Carbon Monoxide" Critical Reviews in Biochemistry and Molecular Biology, 39: 165-195, 2004.

Henstra et al. "Microbiology of synthesis gas fermentation for biofuel production." Current opinion in biotechnology, 18(3), 200-206, 2007.

\* cited by examiner

MICROBIAL ALCOHOL PRODUCTION PROCESS

CROSS REFERENCE TO RELATED APPLICATIONS

This application is a National Stage of International Application No. PCT/NZ2009/000023, filed Feb. 18, 2009, which claims the priority of U.S. Provisional Application No. 61/036,061, filed Mar. 12, 2008, and U.S. Provisional Application No. 61/084,257, filed Jul. 28, 2008.

FIELD

The present invention relates to the production of alcohols by microbial fermentation, particularly to production of alcohols by microbial fermentation of substrates comprising CO. It more particularly relates to processes for the production of alcohols from their corresponding acids.

BACKGROUND

Alcohols are of use in many industries including the perfume, pharmaceutical and fuel industries. Ethanol and butanol, for example, are rapidly becoming major liquid transport fuels around the world. Processes for the production of various alcohols are known. Industrial alcohol production is largely synthetic, deriving from petrochemical processes. However, microbial fermentation can also be used to produce alcohols, for example biofuels, and is becoming increasingly popular.

Biofuels for transportation are attractive replacements for gasoline and are rapidly penetrating fuel markets as low concentration blends. Biofuels, derived from natural plant sources, are more environmentally sustainable than those derived from fossil resources (such as gasoline), their use allowing a reduction in the levels of so-called fossil carbon dioxide ($CO_2$) gas that is released into the atmosphere as a result of fuel combustion. In addition, biofuels can be produced locally in many geographies, and can act to reduce dependence on imported fossil energy resources. Alcohols suitable for use as biofuels include ethanol, butanol and 2,3-butanediol, among others.

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to continue to grow sharply in future, due to an increased interest in ethanol in Europe, Japan, the USA and several developing nations.

For example, in the USA, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, or as a pure fuel in its own right. Also, in Europe, environmental concerns surrounding the consequences of Green House Gas (GHG) emissions have been the stimulus for the European Union to set member nations a mandated target for the consumption of sustainable transport biofuels.

Butanol may also be used as a fuel in an internal combustion engine. It is in several ways more similar to gasoline than it is to ethanol. As the interest in the production and application of environmentally sustainable fuels has strengthened, interest in biological processes to produce butanol (often referred to as bio-butanol) has increased. Butanol may be produced by microbial fermentation of biomass from crops such as sugar beet, corn, wheat and sugarcane. However, the cost of these carbohydrate feed stocks is influenced by their value as human food or animal feed and the cultivation of starch or sucrose-producing crops for butanol production is not economically sustainable in all geographies. Therefore, it is of interest to develop technologies to convert lower cost and/or more abundant carbon resources into fuel butanol.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al, *Archives of Microbiology* 161, pp 345-351 (1994)).

However, ethanol production by micro-organisms by fermentation of gases is typically associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions. Other waste products, such as butyric acid/butyrate may also be produced during commonly used fermentation processes.

Furthermore, biological fermentation processes, which typically utilise yeast or bacteria, may be limited to the production of one or two alcohols which a particular organism is able to produce from the substrate on which it is grown (for example a carbohydrate or gas comprising carbon monoxide). If one wishes to produce a different alcohol, a different micro-organism may be required to be sourced. In many cases, one may not be able to source a bacteria capable of producing the desired alcohol. Therefore, it is of interest to develop technologies to convert lower cost and/or more abundant carbon resources such as organic acids, into desirable products, such as fuel ethanol.

Processes for the microbial conversion of acids to their corresponding alcohols have been described previously: U.S. Pat. No. 4,851,344; White and Simon, Arch Microbiol (1992) 158: 81-84; Huber et al, Arch Microbiol (1995) 164: 110-118. However, these methods also suffer from a number of disadvantages. For example, they require the use of chemical mediators many of which are toxic and/or expensive. In addition, the methods use cell extracts, or isolated cells which are dormant and are required to be spun down and resuspended in buffer prior to conversion of the acids to alcohols. These processing steps are labour intensive and increase the risk of the microbes being exposed to oxygen, lysed or otherwise damaged.

The present invention provides processes for producing valuable alcohols by anaerobic bacterial fermentation that overcome certain disadvantages of the methods known in the art, or at least to provide the public with a useful choice.

STATEMENT OF INVENTION

In one broad aspect, the invention provides a method for converting an acid to its corresponding alcohol using metabolically active bacteria growing on a substrate comprising carbon monoxide and/or hydrogen.

In particular embodiments, the method includes:
a. culturing in a bioreactor, one or more strains of a carboxydotrophic bacteria in the presence of a substrate comprising CO to produce one or more acids and optionally one or more alcohols; and
b. perturbing the microbial culture, such that at least one acid is converted to at least one alcohol.

Typically, at least a portion of the acid(s) produced in step (a) is converted to alcohol(s) in step (b). Additionally or alternatively, additional acid can be added to the bioreactor during step (a) and/or step (b) and converted to at least one alcohol.

In certain embodiments, perturbing the microbial culture includes one or more of:
  altering pH of a liquid nutrient medium containing the microbial culture;
  altering ORP of a liquid nutrient medium containing the microbial culture;
  adding one or more acids to the bioreactor;
  adding one or more reducing agents to the bioreactor;
  altering the CO concentration in a liquid nutrient medium containing the microbial culture;
  altering CO partial pressure in the bioreactor, wherein the substrate comprising CO is gaseous.

In particular embodiments, the step of altering the CO concentration includes increasing the CO concentration in the liquid nutrient medium by at least 1 mmol.

In another broad aspect, the invention provides a method for the production of an alcohol, the method comprising at least the steps of:
  (a) culturing in a bioreactor one or more strains of bacteria in the presence of a substrate comprising carbon monoxide;
  (b) adding an acid to the bioreactor when the one or more strains of bacteria are in a conversion phase to produce the acid's corresponding alcohol; and,
wherein the alcohol produced is not an alcohol which the one or more strains of bacteria are capable of producing when growing on said substrate in the absence of said acid.

In particular embodiments of the above aspects, the method is conducted in the absence of a mediator.

In one embodiment, two or more acids are added to the bioreactor to produce two or more corresponding alcohols.

In certain embodiments, the one or more bacteria are bacteria which are capable of using the aldehyde oxido-reductase (AOR) pathway to reduce an acid to its corresponding alcohol. Appropriate bacteria include species of the genera *Clostridia*, *Moorella*, *Eubacteria*, *Acetobacteria*, *Butyribacterium* and *Desulfobacterium*. In a particular embodiment the bacteria is *Clostridium autoethanogenum*.

Typically, the acid is a monocarboxylic or dicarboxylic acid. In particular embodiments the acid is chosen from acetic acid, propionic acid, n-butyric acid, n-pentanoic acid, n-hexanoic acid, and benzoic acid.

In particular embodiments, the alcohol produced is chosen from ethanol, 1-propanol, 1-butanol, 1-pentanol, 1-hexanol, and benzyl alcohol.

In another broad aspect, the invention provides a method for the production of butanol the method comprising at least the steps of:
  (a) culturing in a bioreactor one or more strains of bacteria which are adapted to produce an alcohol other than butanol in the presence of a substrate comprising carbon monoxide;
  (b) producing butanol by adding butyrate to the bioreactor when the one or more strains of bacteria is actively producing the alcohol other than butanol.

In another broad aspect, the invention provides a method for the production of butanol the method comprising at least the steps of:
  (a) culturing in a bioreactor one or more strains of bacteria which are adapted to produce ethanol in the presence of a substrate comprising carbon monoxide;
  (b) producing butanol by adding butyrate to the bioreactor when the one or more strains of bacteria is actively producing ethanol.

In another broad aspect, the invention provides a method for the production of an alcohol the method comprising at least the steps of:
  (a) culturing in a bioreactor *Clostridium autoethanogenum* in the presence of a substrate comprising carbon monoxide;
  (b) adding an acid to the bioreactor when *Clostridium autoethanogenum* is in a conversion phase to produce the acid's corresponding alcohol; and,
wherein the alcohol produced is not an alcohol which *Clostridium autoethanogenum* is capable of producing when growing on said substrate in the absence of said acid.

In a preferred broad aspect, the invention provides a method for the production of butanol the method comprising at least the steps of:
  (a) culturing in a bioreactor *Clostridium autoethanogenum* in the presence of a substrate comprising carbon monoxide;
  (b) adding butyrate to the bioreactor when *Clostridium autoethanogenum* is in a conversion phase to produce butanol.

The methods of the invention are typically conducted in the absence of a mediator.

In particular embodiments, the acid added to a bioreactor in accordance with the methods of the invention is produced by microbial fermentation of a substrate comprising carbon monoxide.

In certain embodiments, the bacteria are cultured in a liquid media in the absence of yeast extract and/or peptone. In one embodiment, the media is LM23 or LM33 as herein after described.

In another broad aspect, the invention provides a method for producing one or more alcohols the method comprising at least the steps of:
  (a) In a first bioreactor fermenting a substrate to produce one or more acids;
  (b) In the second bioreactor culturing one or more strains of bacteria in the presence of a substrate comprising carbon monoxide;
  (c) Introducing the one or more acids from (a) into the second bioreactor at a time when the one or more strains of bacteria are in a solventogenic phase to produce the alcohols corresponding to the one or more acids; and,
wherein the alcohol produced is not an alcohol which the one or more strains of bacteria are capable of producing when growing on said substrate in the absence of said acid.

In particular embodiments, the method is conducted in the absence of mediator.

In certain embodiments the one or more strains of bacteria in the second bioreactor are as defined herein before.

In another aspect of the invention, there is provided a method for producing alcohols from the anaerobic bacterial fermentation of an acid in a bioreactor, in the presence of a substrate comprising CO.

In one embodiment, the substrate is provided at a CO concentration such that acid to alcohol conversion is promoted.

In one embodiment, the concentration of CO is above a sufficient threshold concentration, such that acid to alcohol conversion is promoted. Providing CO to the fermentation above this sufficient threshold concentration reduces or prevents production of acid and/or reduces or prevents microbial growth, while promoting acid to alcohol conversion.

In one embodiment, the substrate is provided at a CO concentration in a fermentation media of at least about 2.5 mmol/L. In one embodiment, the CO concentration is at least about 2.75 mmol/L. In one embodiment, the CO concentration is at least about 3 mmol/L. In one embodiment, the concentration is at least about 3.5 mmol/L.

Those skilled in the art will appreciate upon consideration of this disclosure that there are many methods for increasing the solubility of CO in fermentation media, including without limitation temperature variation and/or the addition of solubilising agents such as oils. Such methods can be employed in the practice of the present invention as necessary or desirable to achieve a particular CO concentration in the fermentation media.

In one embodiment, the substrate comprising CO is a gaseous substrate, and the amount of CO dissolved in a fermentation media is proportional to CO partial pressure in the fermentation. As such, the sufficient threshold concentration in the fermentation media may be achieved by increasing CO partial pressure. In one embodiment, the gaseous substrate is provided such that the CO partial pressure is at least about 37 psi. In another embodiment, the CO partial pressure is at least about 47 psi.

In accordance with the methods of the invention, additional acid can be supplied to the bioreactor and converted into alcohol.

In various embodiments of the invention, the method includes a step of capturing and recovering one or more alcohols produced by the fermentation.

In another aspect of the invention, there is provided a method of producing alcohols and/or acids, the method including anaerobically fermenting a first substrate in a bioreactor to produce one or more products including alcohols and/or acids; wherein a second substrate comprising CO is added at a desired time point such that the production of alcohol, such as ethanol, relative to acid, such as acetate, increases.

In one embodiment, adding the second substrate comprising CO results in at least a portion of the acid being converted into alcohol, provided the resulting dissolved CO concentration is at or above a sufficient threshold concentration for that fermentation.

In one embodiment, the first substrate also includes CO; however, the method is not limited to such embodiments. For example, in some embodiments, the first substrate may include one or more carbohydrates or pyruvate. Suitable carbohydrates may include but are not limited to cellulose, cellulose hydrolysate, starch, starch hydrolysate, glucose, fructose, xylose, arabinose, or lactose. In some embodiments, the carbohydrate is fructose or xylose. In other embodiments, the first substrate may comprise $CO_2$ and/or $H_2$ or any other components suitable for producing acids and/or alcohols by fermentation.

In various embodiments, the method includes the step of capturing and recovering one or more alcohols produced by the fermentation.

In another aspect of the invention, there is provided a method of producing alcohols and/or acids, the method including the steps of:

(a) providing a substrate comprising CO at a first concentration to a bioreactor containing a culture of one or more micro-organisms; and
(b) anaerobically fermenting the culture in the bioreactor to produce one or more products including alcohols and/or acids from said substrate, wherein the concentration of the substrate provided to the bioreactor may optionally be increased at a desired time point, such that the production of alcohols relative to acids increases.

In various embodiments, increasing the concentration of the substrate results in at least a portion of the acid being converted into alcohol and/or the concentration of the substrate can be increased above a sufficient threshold, wherein at least a portion of the acid is converted into alcohol.

In various embodiments, the method includes the step of capturing and recovering one or more products produced by the fermentation.

In another aspect of the invention, there is provided a method of producing alcohols and/or acids, the method including the steps of:

(a) providing a gaseous substrate comprising CO at a first CO partial pressure in a bioreactor containing a culture of one or more micro-organisms; and
(b) anaerobically fermenting the culture in the bioreactor to produce one or more products including ethanol and/or acetic acid from said substrate, wherein the CO partial pressure may optionally be increased at a desired time point such that the production of ethanol relative to acetate increases.

In one embodiment, the method includes monitoring microbial growth and/or the concentration of one or more products and/or CO concentration, wherein at a desired product and/or CO concentration, the CO partial pressure may be increased. In one embodiment, the CO partial pressure may be increased above 27 psi.

In various embodiments, increasing the CO partial pressure results in at least a portion of the acid being converted into alcohol and/or the CO partial pressure may be increased above a sufficient threshold, wherein at least a portion of the acid is converted into alcohol.

In various embodiments, the method includes the step of capturing and recovering alcohol produced by the fermentation.

According to another aspect of the invention, there is provided a method of regulating microbial growth and/or acid production, the method including the steps of:

(a) providing a gaseous substrate comprising CO at a first CO partial pressure in a bioreactor containing a culture of one or more micro-organisms; and
(b) anaerobically fermenting the culture in the bioreactor to produce one or more products including ethanol and/or acetic acid from said substrate, wherein the CO partial pressure may be increased at a desired time point such that the microbial growth and/or acid production is reduced or substantially inhibited.

In various embodiments, increasing the CO partial pressure results in at least a portion of the acid being converted into alcohol and/or the CO partial pressure may be increased above a sufficient threshold, wherein at least a portion of the acid is converted into alcohol.

In one embodiment, microbial growth and/or acid production may be increased/promoted (or restarted) when the partial pressure of CO is reduced.

In various embodiments, the method includes the step of capturing and recovering alcohol produced by the fermentation.

In another aspect of the invention, there is provided a method of regulating alcohol production, the method including the steps of:

(a) providing a gaseous substrate comprising CO at a first CO partial pressure in a bioreactor containing a culture of one or more micro-organisms;
(b) anaerobically fermenting the culture in the bioreactor to produce one or more products including ethanol and/or acetic acid from said substrate;
(c) increasing the CO partial pressure above a sufficient threshold, such that at least a portion of the acid is converted into ethanol; and
(d) optionally thereafter reducing the CO partial pressure below the threshold such that microbial growth and acid production are promoted.

In various embodiments, production of the alcohol and acid and/or microbial growth can be monitored throughout the fermentation and/or steps (c) and (d) are repeated at least once.

Embodiments of the invention find particular application in the fermentation of acids in the presence of a gaseous substrate comprising CO. The substrate may comprise a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. In one embodiment of the invention, the gaseous substrate is syngas. In one embodiment, the gaseous substrate comprises a gas obtained from a steel mill.

The CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In various embodiments, the fermentation is carried out using a culture of one or more strains of carboxydotrophic bacteria. In various embodiments, the carboxydotrophic bacterium is selected from *Clostridium, Moorella, Oxobacter, Peptostreptococcus, Acetobacterium, Eubacterium* or *Butyribacterium*. In one embodiment, the carboxydotrophic bacterium is *Clostridium autoethanogenum*.

The methods of the invention can be used to produce any of a variety of alcohols, including without limitation ethanol and/or butanol, by anaerobic fermentation of acids in the presence of substrates, particularly gaseous substrates containing carbon monoxide. The methods of the invention can also be applied to aerobic fermentations, to anaerobic or aerobic fermentations of other products, including but not limited to isopropanol, and to fermentation of substrates other than carbon containing gases.

The invention may also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

FIGURES

These and other aspects of the present invention, which should be considered in all its novel aspects, will become apparent from the following description, which is given by way of example only, with reference to the accompanying Figures, in which:

FIG. 1: Conversion of Butyrate into Butanol by *C. autoethanogenum* in serum bottles. Starting conditions: active culture of *C. autoethanogenum*, producing acetate (4.7 g/l) and ethanol (1.2 g/l) pH 5.5, headspace: 25 psig overpressure of 95% CO in CO2. End conditions: pH 6.35, acetate (4.7 g/l), ethanol (3.2 g/l), headspace: 14 psig overpressure.

Figure 2:
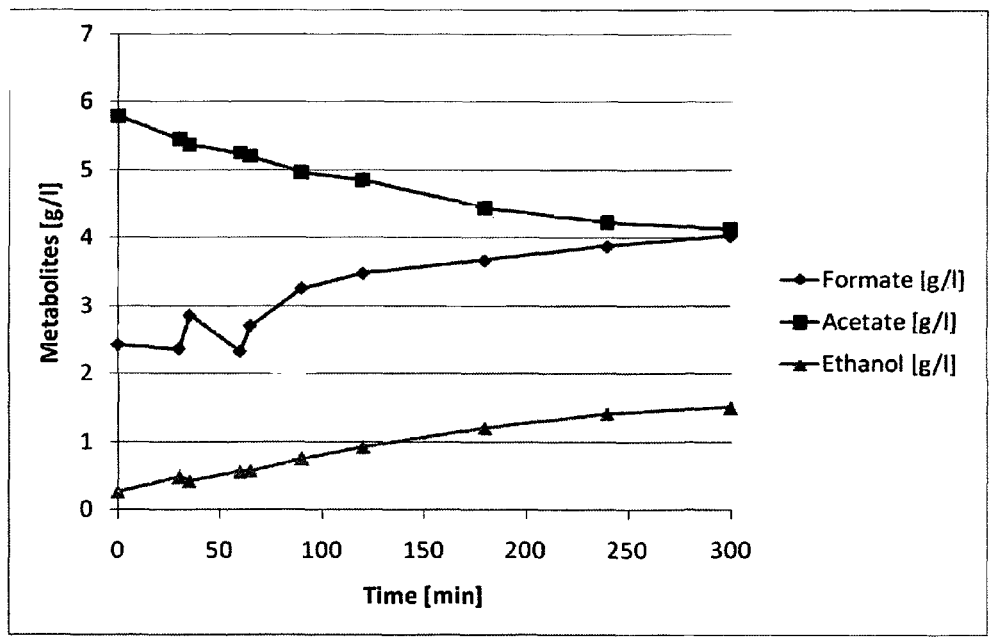

FIG. 2: Effect of formate addition on a batch culture of *Clostridium autoethanogenum* producing acetate and minimal ethanol. Formate solution was added at t=0 and t=30 min (approx) then continuously at t=60 min (approx).

Figure 3:
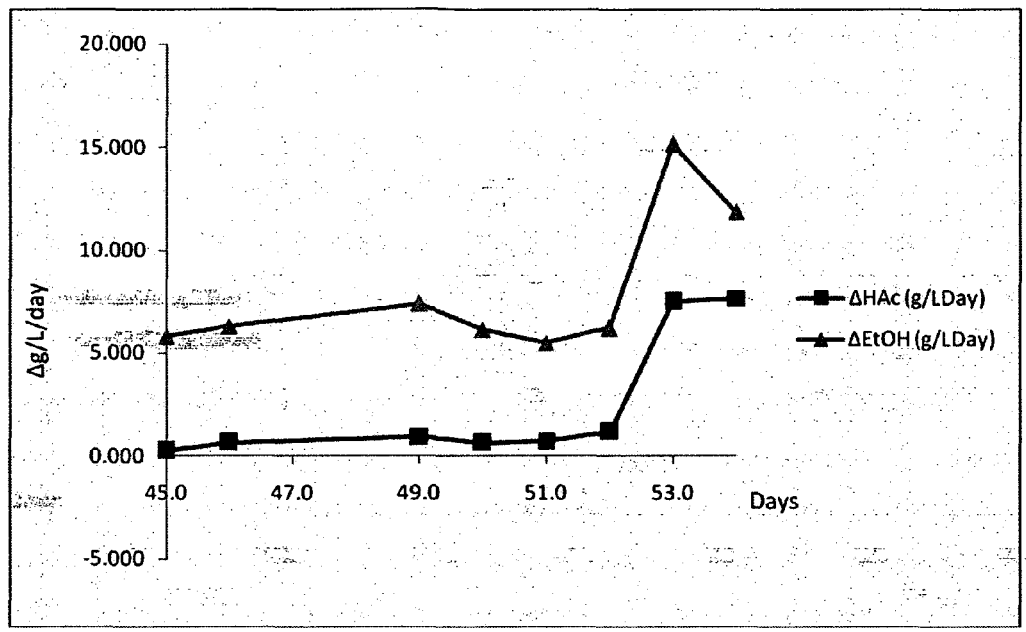

FIG. 3: Effect of acetate addition on a continuous culture of *Clostridium autoethanogenum* producing approximately 6 g/L/day ethanol and 1 g/L/day acetate. Acetate (15 g/L/day) was added continuously from day 52.

Figure 4:
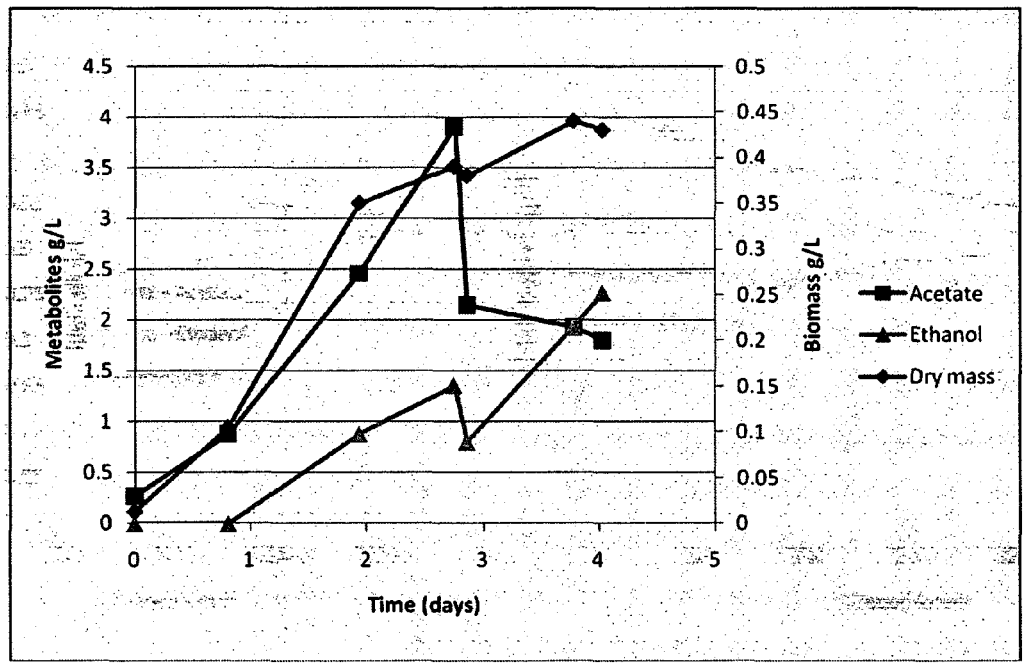

FIG. 4: Effect of pH change on a microbial culture comprising *Clostridium autoethanogenum* producing acetate and ethanol. Cell recycle was initiated for approximately 2 hours then pH was adjusted to 5.9 at approximately t=3 days. Following pH change, acetate was consumed and increased amounts of ethanol were produced.

Figure 5:
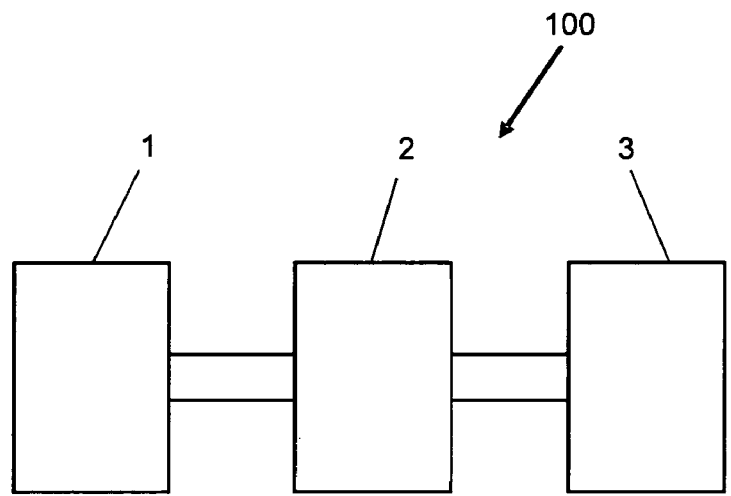

FIG. 5: A system including a growth bioreactor and a conversion bioreactor according to particular embodiments of the invention.

Figure 6:
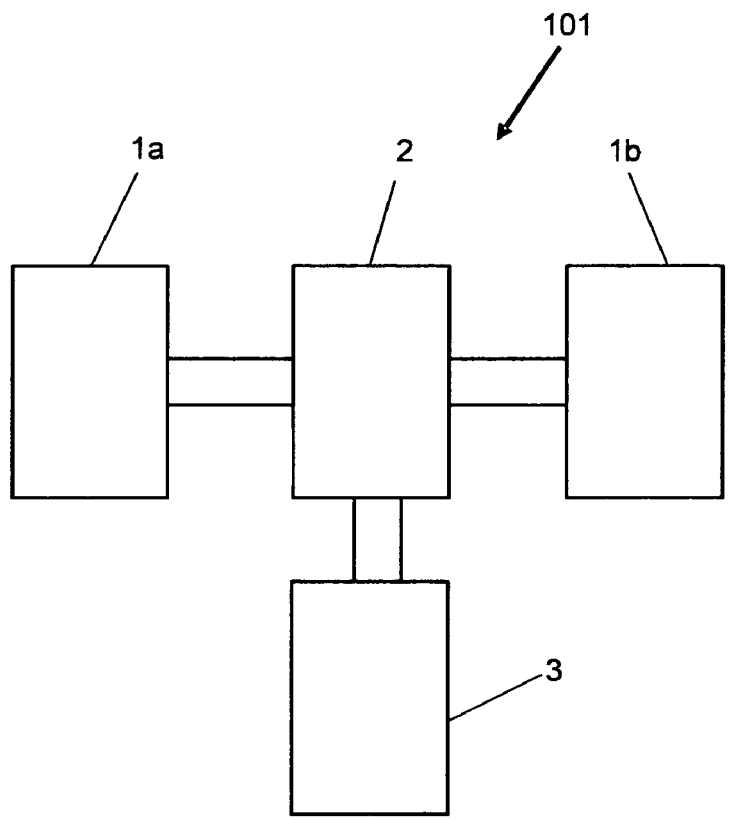

FIG. 6: A system including multiple growth bioreactors and a conversion bioreactor according to particular embodiments of the invention.

EMBODIMENT(S) OF THE INVENTION

The following is a description of the present invention, including various embodiments thereof, given in general terms. The invention is further exemplified in the disclosure given under the heading "Examples" herein below, which provides experimental data supporting the invention, specific examples of aspects of the invention, and illustrative means of performing the invention.

Products including acids and alcohols can be produced from a substrate comprising CO by a microbial culture. In accordance with the methods of the invention, perturbation of the microbial culture surprisingly results in consumption of acids with concomitant production of alcohols by the microbial culture. It is considered that this result may be due to at least a portion of the acid present in the fermentation broth being directly or indirectly reduced to alcohol, particularly ethanol. This can be referred to as the "conversion phase" of the fermentation reaction. In accordance with the methods of the invention, a fermentation reaction can be switched from a production (or growth) phase, where microbial growth is promoted and alcohols and/or acids are produced, to the conversion phase by perturbing the microbial culture.

It is recognised that at least a portion of the microbial culture may be in a production phase while at least a portion is in a conversion phase. However, on perturbation, at least a portion of the microbial culture in the production phase switches to the conversion phase, such that the production of alcohols relative to acids increases. In a particular embodiment, there is an overall net consumption of acid(s) and production of alcohol(s).

In accordance with one embodiment of the invention, ethanol is produced by microbial fermentation when a microbial culture producing product(s), such as acetate and optionally ethanol, from a substrate comprising CO is perturbed. At least a portion of the CO may be converted to acids and/or alcohols following perturbation, but the majority of the ethanol is produced by microbial reduction of the acetic acid/acetate ('conversion').

There are many examples of fermentation reactions using substrates comprising CO to produce alcohols and/or acids, where alcohols and acids are produced at the same time. However, in such examples, the product ratio generally favours acid (i.e. acetic acid/acetate) over alcohol (ethanol). In another embodiment of the invention, particular fermentation conditions may favour alcohol production over acid production. Under such conditions, additional acid added to the fermenter can be converted to the corresponding alcohol by the microbial culture. For example, acids such as butyric acid can be added to the fermentation reaction and converted to alcohols such as butyrate.

In accordance with the methods of the invention, it has been surprisingly found that it is not necessary to use a mediator, such as methyl viologen, to assist the conversion of acid(s) to alcohol(s). In fact, it has been identified that methyl viologen, has a negative effect on butanol production by *C. autoethanogenum*. This is in contrast to reports that a mediator is required for microbial conversion of acids to their corresponding alcohols.

Whilst not wishing to be bound by any particular theory, it is considered that the conversion of acids to alcohols by *Clostridium autoethanogenum* in accordance with the invention occurs via a biochemical pathway involving the enzyme aldehyde oxido-reductase (AOR). AOR is a unique tungsten-containing enzyme able to reduce non-activated carboxylic acids to aldehydes. The aldehyde can be furthered reduced by aldehyde dehydrogenases to alcohol. AOR represents an important branch of the solventogenesis pathway. The tungsten cofactor has been shown to be crucial for enzyme activity. These enzymes can be found in fermentative microorganisms such as *Clostridium, Desulfitobacterium*, and *Pyrococcus*. The best characterized AORs belong to *Pyrococcus furiosus* whose genome contains five of which four have been characterized. The first AOR of *P. furiosus* has a broad substrate range but favours aldehydes derived from amino acids. Its crystal structure revealed the presence of a molybdopterin-based tungsten binding site. The second AOR, glyceraldehyde-3-phosphate ferredoxin oxidoreductase (GFOR), only utilizes glyceraldehydes-3-phosphate and the third AOR, formaldehyde ferredoxin oxidoreductase (FOR), prefers one to three carbon aldehydes. The fourth AOR, WOR5, has a broad substrate range. AOR have also been purified from *Clostridium formicoaceticum* and *thermoaceticum*.

*Clostridium autoethanogenum* contains two putative AOR genes sharing ~56% identity with AOR of *P. furiosus* and ~80% with *Clostridium botulinum*. The AOR genes mark a significant difference from *C. autoethanogenum*'s closest sequenced relative, *Clostridium kluyveri*, whose genome does not contain AOR genes and alcohol production proceeds via acetyl-CoA. It is contemplated that the results obtained are applicable to the production of any alcohol from its corresponding acid using *Clostridium autoethanogenum* or any other bacterium capable of using the AOR pathway.

Thus, in its broadest aspect, the invention provides a method for converting an acid to its corresponding alcohol using a microbial culture. In particular embodiments, the microbial culture converts the acid to the alcohol in the presence of a substrate comprising CO and/or H2.

DEFINITIONS

Unless otherwise defined, the following terms as used throughout this specification are defined as follows:

As used herein the term "conversion phase" is intended to refer to a period of time during which bacteria are fermenting one or more acid(s) to produce one or more alcohol(s). Typically at least a portion of a bacterial population will be in such a phase. However, it is not necessary for all bacteria in a population to be actively producing alcohol. The conversion phase is characterised by the presence of a level of alcohol in the fermentation broth.

The term "perturb", "perturbation" and the like, as used herein in relation to a microbial culture, is intended to include any alteration made that directly or indirectly affects the microbial culture. Alterations made to the microbial culture include changing fermentation operating conditions such as pH, CO concentration, ORP or altering the composition of a liquid nutrient medium containing the culture.

The term "microbial culture" and the like, as used herein is intended to include at least one micro-organism supported in and/or on a nutrient medium suitable to promote growth and/or metabolite production.

As mentioned herein, the "alcohol produced" by a process of the invention is not an alcohol which the one or more strains of bacteria are capable of producing when growing on the substrate in the absence of the corresponding acid. However, it should be appreciated that the methods may produce additional products; for example, an acid or alcohol which the bacteria ferments from the substrate on which it is cultured. The "alcohol produced" by the method may be referred to as the "primary alcohol" or "primary product" and any additional products as "co-products". Use of "primary" should not be taken to imply a particular level of product compared to co-products.

"Redox mediator(s)" and the like, as used herein is intended to refer to an electron shuttle that acts as a reversible electron donor and/or electron acceptor. Mediators include viologen dyes (such as methyl viologen), anthraquinone and other quinone dyes, triphenylmethane dyes, phthalocyanimes, methine dyes, pyrrole dyes, porphyrin dyes, pteridines, pteridones, flavines, and metal complexes of secondary groups VI, VII and VIII.

The use of term "acid", "acids" and the like when referring to adding an "acid" to a culture or bioreactor in accordance with the invention should be taken broadly, including any monocarboxylic and dicarboxylic acids. In addition reference to addition of "acids(s)" should be taken to include reference to the equivalent salt or a mixture of salt and acid. Similarly, references to specific acids herein should be taken to include reference to equivalent salts (for example butyric acid and butyrate) and vice versa. The ratio of molecular acid to carboxylate in the fermentation broth is dependent upon the pH of the system. Exemplary acids include acetic acid, propionic acid, n-butyric acid, n-pentanoic acid, n-hexanoic acid, and benzoic acid.

The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Membrane Reactor such as Hollow Fibre Membrane Bioreactor (HFMBR), Static Mixer, or other vessel or other device suitable for gas-liquid contact.

As will be described further herein, in some embodiments the bioreactor may comprise a first growth reactor and a second fermentation reactor. As such, when referring to the addition of one or more carbohydrates to the bioreactor or fermentation reaction it should be understood to include addition to either or both of these reactors where appropriate.

The term "substrates comprising carbon monoxide" include any solid, liquid or gaseous material containing CO that may be introduced into a bioreactor for fermentation. "Gaseous substrates comprising carbon monoxide" include any gas which contains carbon monoxide. The gaseous substrate will typically contain a substantial proportion of CO, such as, for example, at least about 15% to about 95% CO by volume.

The term "dissolved CO concentration" includes the amount of CO present in a fermentation broth/media as a function of volume.

The term "CO partial pressure" and the like include the relative pressure exerted on a system by CO in a gaseous substrate including CO and optional additional gases.

The phrase "threshold concentration", "sufficient threshold concentration" and the like can be quantitatively defined but may vary under different fermentation conditions, such as those employed with different microbes; the term includes the concentration or concentration range at which a microbe switches from substantially producing alcohol and/or acid from a substrate, to producing alcohol and consuming acid for an extended period.

Unless the context requires otherwise, the phrases "fermenting", "fermentation process" or "fermentation reaction" and the like, as used herein, are intended to encompass both the growth phase and product biosynthesis phase of a process involving the growth/and or biosynthesis of a product by a micro-organism.

In accordance with the methods of the invention, products including acids and alcohols are produced from a substrate comprising CO, for example, a gaseous substrate comprising CO, by microbial fermentation. In particular embodiments of the invention, an actively growing microbial culture producing products such as acid(s) and optionally alcohol(s) can be perturbed such that at least a portion of the microbial culture consumes one or more acid(s) and produces one or more corresponding alcohol(s). This result may be due to at least a portion of the acid present in the fermentation broth being directly or indirectly reduced to alcohol, particularly ethanol. This can be referred to as the "conversion phase" of the fermentation reaction. In accordance with particular embodiments of the invention, a fermentation reaction can be switched from a substantially production phase, where microbial growth is promoted and alcohols and/or acids are produced, to the conversion phase increasing CO concentration in the fermentation reaction.

In another embodiments of the invention, at least a portion of an actively growing culture may be producing alcohol(s) and the perturbation includes adding one or more acid(s) to the culture such that at least a portion of the one or more acid(s) are converted to one or more alcohol(s).

Generally, the methods of the invention comprise at least
(a) culturing in a bioreactor one or more strains of bacteria in the presence of a substrate comprising carbon monoxide to produce one or more acids and optionally one or more alcohols, and
(b) perturbing the cultured bacteria, such that at least one acid is converted to at least one alcohol.

In particular embodiments, at least a portion of the acid produced by the bacteria during step (a) is converted to the corresponding alcohol in step (b). However, in particular embodiments, additional acid(s) can be added to the bioreactor, such that at least a portion of the added acid(s) are converted to alcohol(s) in step (b). In such embodiments, the alcohol produced may not be an alcohol which the one or more strains of bacteria are capable of producing when growing on the substrate in the absence of the acid. The method is preferably conducted in the absence of a mediator.

In a particular embodiment the method comprises at least the steps of
a) culturing in a bioreactor one or more strains of bacteria in the presence of a substrate comprising carbon monoxide, wherein the bacteria are producing alcohol(s); and
b) adding acid to the cultured bacteria when at least a portion of the culture is in a conversion phase to produce alcohol.

There are many examples of fermentation reactions using substrates comprising CO to produce alcohols and/or acids, where alcohols and acids are produced at the same time. However, in such examples, the product ratio generally favours acid (i.e. acetic acid/acetate) over alcohol (ethanol).

Suitable perturbations for switching a microbial culture from a production phase to a conversion phase include but are not limited to: changing pH and/or ORP of a fermentation media; changing CO concentration in a fermentation broth (those skilled in the art will appreciate there are multiple methods of achieving this depending on the fermentation method including altering gas composition, altering gas pressure, altering gas flow rate, altering agitation speed in a CSTR); adding reducing agent; adding one or more acids.

Accordingly, in particular embodiments of the invention, perturbing the microbial culture includes one or more of:
altering pH of a liquid nutrient medium containing the microbial culture;
altering ORP of a liquid nutrient medium containing the microbial culture;
adding one or more acids to the bioreactor;
adding one or more reducing agents to the bioreactor;
altering the CO concentration in a liquid nutrient medium containing the microbial culture;
altering CO partial pressure in the bioreactor, wherein the substrate comprising CO is gaseous.

While the following description focuses on particular embodiments of the invention, it should be appreciated that the invention is applicable to production of alternative alcohols from their corresponding acids. Exemplary alcohols include ethanol, 1-propanol, 1-butanol, 1-pentanol, 1-hexanol, and benzyl alcohol. Exemplary corresponding acids include acetic acid, propionic acid, n-butyric acid, n-pentanoic acid, n-hexanoic acid, and benzoic acid, respectively. Examples of further alcohols which may be produced in accordance with the invention include those of use in the perfume, pharmaceutical and fuel industries.

In addition, the method may be conducted using bacteria other than *C. autoethanogenum*; for example bacterial species of the genera *Clostridia, Moorella, Eubacteria, Acetobacteria, Butyribacterium* and *Desulfobacterium* may be used. More particularly, *Clostridium ljungdahlii, Clostridium aceticum, Clostridium formicaceticum, Moorella thermoacetica, Moorella thermoautotrophica, Eubacterium limosum, Acetobacterium woodii, Butyribacterium methylotrophicum,* and *Desulfobacterium autotrophicum* may be used.

Certain embodiments of the invention are adapted to use gas streams produced by one or more industrial processes. Such processes include steel making processes, particularly processes which produce a gas stream having a high CO content or a CO content above a predetermined level (i.e., 5%). According to such embodiments, carboxydotrophic bacteria are preferably used to produce acids and/or alcohols, particularly ethanol or butanol, within one or more bioreactors. Those skilled in the art will be aware upon consideration of the instant disclosure that the invention may be applied to various industries or waste gas streams, including those of vehicles with an internal combustion engine. Also, those skilled in the art will be aware upon consideration of the instant disclosure that the invention may be applied to other fermentation reactions including those using the same or different micro-organisms. It is therefore intended that the scope of the invention is not limited to the particular embodiments and/or applications described but is instead to be understood in a broader sense; for example, the source of the gas stream is not limiting, other than that at least a component thereof is usable to feed a fermentation reaction. The invention has particular applicability to improving the overall carbon capture and/or production of ethanol and other alcohols from gaseous substrates such as automobile exhaust gases and high volume CO-containing industrial flue gases.

Fermentation

Processes for the production of ethanol and other alcohols from gaseous substrates are known. Exemplary processes include those described for example in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of anaerobic bacteria are known to be capable of carrying out the fermentation of CO to alcohols, including n-butanol and ethanol, and acids such as acetic acid, and are suitable for use in the process of the present invention. Examples of such bacteria that may be suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella sp* HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp 41-65). In addition, it should be understood that other carboxydotrophic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

In some embodiments, where the substrate is gaseous, it may be desirable to conduct the production and/or conversion phase(s) at elevated pressure; which may be at least several atmospheres. Such systems will employ the use of a bioreactor adapted to withstand elevated pressure. Many types of bioreactors may be adapted to withstand higher pressures; an example of such a bioreactor is the Buchi AUTOKLAV™ reactor.

In some embodiments of the invention, the bioreactor may comprise a first, growth reactor in which the micro-organisms are cultured and optionally acids are produced, and a second, fermentation reactor, to which broth from the growth reactor is fed and in which additional, if not most of, the alcohol fermentation product (ethanol, for example) is produced. As noted above, a pressure rated fermentation bioreactor may be employed.

According to various embodiments of the invention, the carbon source for the fermentation reaction is a gaseous substrate containing CO. The substrate may be a CO-containing waste gas obtained as a by-product of an industrial process, or from some another source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing substrate may be captured from the industrial process before it is emitted into the atmosphere, using any convenient method. Depending on the composition of the CO-containing substrate, it may also be desirable to treat it to remove any undesired impurities, such as dust particles before introducing it to the fermentation. For example, the gaseous substrate may be filtered or scrubbed using known methods.

Alternatively, the CO-containing substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of H2:CO. In other embodiments, the substrate stream comprises low concentrations of H2, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemistry and Biotechnology* Volume 101, Number 3/October, 2002) could be used for this purpose.

In one embodiment of the invention, products are produced by fermentation of a first substrate and a second substrate. In one particular embodiment of the invention, alcohols and/or acids will be produced when a first substrate, such as pyruvate or a carbohydrate such as fructose or xylose, and a second substrate, such as a substrate comprising CO, are provided. When the fermentation is perturbed, at least a portion of the acids (acetic acid/acetate) are converted to alcohols (ethanol). It will be appreciated upon consideration of the present disclosure, that there are many examples of carbohydrates suitable for fermentation known in the art and many examples of the types of processes used to ferment the carbohydrate substrate applicable to the methods of the invention. By way of example, suitable substrates may include, but are not limited to, monosaccharides such as glucose and fructose, oligosaccharides such as sucrose or lactose, polysaccharides, such as cellulose or starch. Although all of these carbohydrate substrates (and mixtures thereof) are suitable for use in various embodiments of the present invention, carbohydrate substrates that may be more commonly used include glucose, fructose, xylose and sucrose (and mixtures thereof).

Those skilled in the art will appreciate from consideration of this disclosures that fermentable sugars suitable for use in the present methods may be obtained from cellulosic and lignocellulosic biomass through processes of pre-treatment and saccharification, as described, for example, in US patent application publication 2007/0031918. Biomass refers to any cellulose or lignocellulosic material and includes materials comprising cellulose, and optionally further comprising hemicellulose, lignin, starch, oligosaccharides and/or monosaccharides. Biomass includes, but is not limited to bioenergy crops, agricultural residues, municipal solid waste, industrial solid waste, sludge from paper manufacture, yard waste, wood and forestry waste.

In one embodiment of the invention, commercially available fructose or xylose are used as optional carbon and energy sources for the fermentation.

It will be appreciated that for growth of the bacteria and CO-to-product fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/115157 and WO2008/115080 referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO07/117,157 and WO08/115,080.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-product conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

In particular embodiments of the invention, ethanol is produced by microbial fermentation when the system is perturbed in closed vessels. In several examples provided herein, the pH of the fermentation is uncontrolled and on conversion of acid to alcohol, the pH increases. In such examples, the pH increases to around 6.5 and may have an inhibitory effect on the conversion; those of skill in the art will appreciate that the methods of the invention can include pH control of the fermentation media.

Product Recovery

A fermentation in accordance with the methods of the invention will result in a fermentation broth comprising a desirable product (such as ethanol and/or butanol) and/or one or more by-products (such as acetate and butyrate) as well as bacterial cells, in a nutrient medium.

The products of the fermentation reaction can be recovered using known methods. Exemplary methods include those described in WO07/117,157, WO08/115,080, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which is produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol- and acetate-containing, permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

The invention will now be described in more detail with reference to the following non-limiting examples.

Conversion of Acid(s) to Alcohol(s)

In a particular broad aspect, the invention provides a method of converting acid(s) to a corresponding alcohol(s) using a microbial culture. In particular embodiments, the microbial culture converts the acid to the alcohol in the presence of a substrate comprising CO and/or H2.

In accordance with the methods of the invention, a microbial culture comprising one or more carboxydotrophic bacteria can be perturbed such that the microbial culture converts acid(s) to alcohol(s). The methods of the invention are applicable to a range of microbial fermentation reactions which utilise CO as a primary substrate and produce one or more acids and/or alcohols. For example, fermentations to produce acetate, butyrate, propionate, caproate, ethanol, propanol, and butanol can be conducted in accordance with the methods of the invention. The methods of the invention may also be used in producing hydrogen. These products may be produced, for example, by fermentation using carboxydotrophic microbes from the genus *Moorella, Clostridia, Ruminococcus/Peptostreptococcus, Acetobacterium, Eubacterium, Butyribacterium, Oxobacter, Methanosarcina, Methanosarcina,* and *Desulfotomaculum.*

In particular embodiments, the microbial culture comprises acetogenic bacteria, such as *Clostridium autoethanogenum* that typically utilise a substrate comprising CO to produce products including acetate and/or ethanol. In such embodiments, the microbial culture may be grown under desirable conditions in a fermentation broth to promote growth and acetate production. The growth (or production) phase of acetogenic bacteria is typically associated with an increase in cellular matter (biomass accumulation) and acetate production, with little or no concomitant alcohol production. In particular embodiments of the invention, the microbial culture is perturbed such that acids present in the fermentation broth are converted to corresponding alcohols (e.g. acetate to ethanol and/or butyrate to butanol). Conversion of acids to alcohols can be referred to as the conversion phase.

In particular embodiments of the invention, the microbial culture can be perturbed such that acids produced by the culture during the production phase are converted to alcohols. Additionally or alternatively, the microbial culture can be perturbed such that acids not produced by the culture during the production phase are converted to alcohols. For example, alcohols not produced by the microbial culture (such as propionate, butyrate, valerate, hexanoate, isovalerate, 2-methylbutyrate) can be added to the fermentation broth and converted to corresponding alcohols.

In one embodiment of the invention the acid is first fed or added to the fermentation reaction before or during the conversion stage. The acid may optionally be added in single or multiple batches or continuously over a desired time period. The amount of acid added to the bioreactor may vary. However, the inventors contemplate addition of acid in an amount which provides a concentration of approximately 0.1 to 100 g of acid per L of fermentation broth. More preferably, the acid is added in an amount to provide a concentration of from approximately 0.1 to 50 g/L, or 1 to 20 g/L. Further examples of appropriate levels of acid to be added to a bacterial culture are provided in the "Examples" section herein after.

The acid may be added to the bioreactor in a batch, fed-batch, or continuous manner. In one embodiment the acid is added in a fed-batch or continuous manner so as to maintain a concentration of acid in the bioreactor within the range mentioned above.

The acid may be added to the bioreactor in any suitable form, including compositions containing the acid and one or more other ingredients, carriers, or diluents. In one embodiment, the acid is preferably prepared and added to the bioreactor as a stock solution, buffered to pH 5.5.

Acids of use in the invention may be produced by any number of known methods, including microbial fermentation. In one embodiment, the acids are produced by microbial fermentation on substrates comprising carbohydrates or carbon monoxide for example. Preferably they are produced by microbial fermentation on a substrate comprising carbon monoxide, more preferably a gaseous substrate comprising carbon monoxide. Examples of bacteria of use in producing the acids include those of the genera Clostridia, Moorella and Ruminococcus, Eubacteria, Butyribacterium, Oxobacter and Acetobacteria are of use to this end. In preferred embodiments the bacteria are chosen from *Clostridium autoethanogenum, Clostridium ljungdahlii, Clostridium aceticum, Clostridium formicaceticum, Clostridium tetanomorphum, Clostridium carboxidivorans, Moorella thermoacetica, Moorella thermoautotrophica, Ruminococcus productus, Eubacterium limosum, Butyribacterium methylotrophicum, Oxobacter pfennigii,* and *Acetobacterium woodii.* Skilled persons may readily appreciate additional bacteria of use in producing acids applicable to the present invention.

Processes for microbial fermentation to produce acids of use in the invention will be readily appreciated by persons of skill in the art, particularly having regard to the information provided herein. However, by way of example, butyrate may be produced from carbon monoxide containing gases as described by Grethlein et al, 1991 (Journal of Fermentation and Bioengineering, Vol 72, No 1, 58-60).

In one embodiment of the invention the method is a batch-fed or continuous process which links production of a desired acid by microbial fermentation followed by use of that acid to produce its corresponding alcohol in accordance with the methods described herein before. In this embodiment, the method comprises at least the steps of a) in a first bioreactor fermenting a substrate (preferably a substrate comprising carbon monoxide, more preferably a gaseous substrate comprising carbon monoxide) to produce one or more acids, b) in a second bioreactor culturing one or more strains of bacteria in the presence of a substrate comprising carbon monoxide, and c) introducing the one or more acids from (a) into the second bioreactor at a time when the one or more strains of bacteria are in a conversion phase to produce the alcohols corresponding to the one or more acids. In a related embodiment further growth reactors may feed bacteria to the first and/or second bioreactors.

While in particular embodiments the bacteria are cultured in the presence of a substrate comprising carbon monoxide, in alternative embodiments the bacteria may first be grown to a desired density on an alternative substrate, for example one comprising sugars or other carbohydrates. The bacteria can then be transferred to a substrate comprising carbon monoxide for conversion of acids to their corresponding alcohols. This embodiment may be conducted in a two reactor system as described above.

Fermentation reactions utilising a mixed substrate, such as carbohydrate and a gaseous substrate comprising CO can be used to produce alcohols and/or acids. In accordance with the methods of the invention, on perturbation of such fermentation reactions, at least a portion of the acid is consumed, and alcohol production increases.

In accordance with the methods of the invention, alcohols and/or acids may be produced by microbial fermentation of an alternative substrate such as carbohydrates. At a predetermined time point, or on accumulation of an excess amount of acid, CO may be added to the bioreactor and the fermentation reaction optionally further perturbed to convert at least a portion of the acid to alcohol.

It will be appreciated that in order to support growth and conversion by bacteria of use in the invention a suitable nutrient medium will need to be fed to the bioreactor. Persons of skill in the art will readily appreciate media of use in the present invention. However, generally, a nutrient medium will contain vitamins, minerals and metals sufficient to permit growth of the bacteria on substrates comprising CO. In particular the media will include one or more metals which assist the activity of enzymes which may be involved in the conversion of acids to their corresponding alcohols; for example, CODH (CO-dehydrogenase) and AOR enzymes. In one embodiment of the invention, the nutrient media does not contain tryptone nor yeast extract. Anaerobic media suitable for use in the present invention includes the LM23 and LM33 media formulation described herein after under the section headed "examples" herein after.

While a single type of media may be used to support growth and product formation, it should be appreciated that more than one media may be used in a process of the invention. For example, where the process utilises separate growth and fermentation reactors, one media may be utilised in the growth reactor and separate media in the fermentation reactor.

Culturing of the bacteria should desirably be carried out under appropriate conditions to allow conversion of acids to alcohols to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Exemplary conditions are provided in the "examples" section herein after. The optimum reaction conditions will depend partly on the bacteria to be used and the alcohol to be produced.

It is also desirable that the rate of introduction of the CO-containing substrate is such as to ensure that the concentration of CO in the liquid phase does not become limiting. This is because a consequence of CO-limited conditions may be that the product(s) is consumed by the culture.

It will be appreciated by persons of general skill upon consideration of the instant disclosure that a variety of fermentation conditions or parameters may be altered in order to perturb the microbial culture such that at least a portion of the microbial culture switches from a production phase to a conversion phase. For example, a fermentation parameter may be altered such that acids are converted to alcohols by the microbial culture. Suitable perturbations for switching a microbial culture from a production phase to a conversion phase include: changing pH and/or ORP of a fermentation media; changing CO concentration in a fermentation broth (there are multiple methods of achieving this depending on the fermentation method including altering gas composition, altering gas pressure, altering gas flow rate, altering agitation speed in a CSTR); adding reducing agent; adding one or more acids. Those skilled in the art will appreciate suitable methods for achieving the desired perturbation and will also appreciate additional methods for perturbing a microbial culture in accordance with the methods of the invention. However, several exemplary methods are described in the "Examples" section hereinbelow. In particular embodiments of the invention, adding one or more acids to the fermentation broth provides suitable perturbation for at least a portion of the microbial culture to switch from a production phase to a conversion phase. For example, acetate can be added to a microbial culture actively growing and producing acetate and alcohols and the culture converts at least a portion of the added acetate into ethanol.

In one embodiment of the invention, additional acetate can be added to a fermentation reaction continuously producing alcohol and acetate at a rate of approximately 15 g/L/day. Consequently, the culture will convert the acetate to ethanol at a rate of 6-15 g/L/day.

In an alternative embodiment, additional acids can be added in conjunction with at least one other perturbation such as altering fermentation broth CO concentration or adding a reducing agent.

Any suitable reducing agent can be used in accordance with the methods of the invention, however by way of example, dithionite salts (such as sodium dithionite), sulfide salts (such as sodium sulfide) or cysteine and optionally additional acid(s) can be added to a fermentation reaction such that at least a portion of the microbial culture switches from a production phase to a conversion phase, thus converting acid(s) to corresponding alcohol(s). In particular embodiments, sodium sulfide is added to a fermentation reaction that predominantly produces acetate, such that at least a portion of the acetate is converted into ethanol. Those skilled in the art will be able to determine the amount of reducing agent required to perturb the system sufficiently to convert acids to alcohols. However, by way of example reducing agents may be added in the concentration range 0.005 mM to 10 mM or 0.05 mM to 1 mM. In particular embodiments of the invention a redox mediator such as methyl viologen is added in addition to the reducing agent. Addition of the redox mediator has a detrimental effect, thus in accordance with particular embodiments of the invention, the method for converting acid(s) to alcohol(s) is preferably conducted in the absence of a redox mediator.

In another embodiment of the invention, formate is added to a fermentation reaction to switch the microbial culture from the production phase to the conversion phase. In particular embodiments of the invention, 2-5 g/L formate can be added to the microbial culture such that acetate produced by the culture during the production phase is converted into ethanol. In particular embodiments, formate can be added at a rate of approximately 3-6 g/L/day such that at least a portion of acetate produced by the culture is converted into ethanol.

In another embodiment of the invention, the microbial culture can be perturbed by altering pH and/or ORP (open redox potential) of a fermentation media containing a microbial culture, such that acid(s) is converted to alcohol(s). Those skilled in the art will appreciate means and/or methods for altering pH and/or ORP of a fermentation media. However by way of example, pH of a liquid nutrient medium containing a microbial culture can be adjusted using acids (such as hydrochloric acid, sulphuric acid or acetic acid) or bases (such as sodium hydroxide). Similarly, ORP can be adjusted in combination with pH or independently by addition of reducing agents.

In a particular embodiment, pH of a liquid nutrient medium maintained at pH 5.5 is increased to 5.9 by addition of sodium hydroxide such that acetate produced during a production phase is converted into ethanol. On changing the pH, the redox potential of the media reduced from approximately −430 to −470 mV.

In another embodiment of the invention, increasing CO concentration in a bioreactor switches at least a portion of the microbial culture from a production phase to a conversion phase. In certain embodiments, a microbial culture is established in a liquid nutrient medium in a stirred bioreactor such as a CSTR. It is recognised that due to the low solubility of CO, at high cell density (e.g. 0.5-5 g/L) the CO concentration in the liquid nutrient medium will approach zero as the microbial culture consumes the CO at approximately the same rate it is transferred into solution. CO concentration of the liquid nutrient medium can be increased by increasing CO partial pressure according to Henry's law. Thus in accordance with particular embodiments of the invention, the microbial culture is perturbed by increasing the partial pressure of CO in a bioreactor.

In accordance with one embodiment of the invention, ethanol is produced by microbial fermentation when the concentration of CO in the fermentation media is increased. At least a portion of the CO may be converted to acids and/or alcohols during this conversion phase, but the majority of the ethanol may be produced, by microbial reduction of the acetic acid/acetate. It is recognised that some fermentation reactions may be operated at elevated CO partial pressure. As such, in order to increase CO concentration in the fermentation media, the CO partial pressure can be increase by at least 15 psi, or at least 20 psi, or at least 25 psi, or at least 30 psi, or at least 35 psi, or at least 40 psi such that acid(s) are converted to alcohol(s).

In one embodiment of the invention, a substantial portion of the acid in a fermentation broth is converted to alcohol. In some embodiments of the invention, increasing the concentration of CO results in at least 60% of the acid available in the fermentation broth being converted into alcohol. In other embodiments, at least 70% of the acid is converted to alcohol. In other embodiments, at least 80% of the acid is converted to alcohol.

In particular embodiments of the invention, the CO partial pressure is increased to approximately 15.9 psia, or at least 20 psia, or at least 30 psia, or at least 40 psia, or at least 50 psia such that acids are converted to corresponding alcohols. In such embodiments, according to Henry's law, the CO concentration in the liquid nutrient medium is expected to be at least 1 mmol, or at least 1.2 mmol, or at least 1.4 mmol, or at least 1.6 mmol, or at least 1.8 mmol, or at least 2.2 mmol, or at least 2.6 mmol, or at least 3.2 mmol.

In certain embodiments of the invention, the acids are converted to corresponding alcohols at a rate of approximately at least 12 g/L/day, or at least 14 g/L/day, or at least 16 g/L/day, or at least 18 g/L/day, or at least 20 g/L/day, or at least 22 g/L/day, or at least 24 g/L/day in the period after perturbation (e.g. up to 1 hour, or up to 2 h, or up to 3 h, or up to 5 h after perturbation). In particular embodiments, in the presence of hydrogen in addition to CO, the rate of acid to alcohol conversion increases to up to 25 g/L/day, or up to 26 g/L/day, or up to 27 g/L/day following perturbation. However, the rate of conversion slows over time, such that in certain embodiments acid(s) (e.g. acetate) can continue to accumulate over the course of the fermentation reaction.

Increasing the concentration (or partial pressure) of CO in accordance with the methods of the invention promotes acid production and microbial growth. However, when CO concentration (or partial pressure) is increased above a sufficient threshold concentration, acid production and/or microbial growth is substantially inhibited.

Accordingly, in accordance with the methods of the invention, microbial growth and/or acid production can be regulated by adding CO. Thus, the invention provides a means to control the production of products including alcohols and/or acids by microbial fermentation of CO, wherein, on accumulation of an excess of acid in a fermentation broth, the concentration of CO can be increased above a threshold concentration to convert at least a portion of the acid to alcohol.

In one embodiment, the invention provides a method for producing alcohols from the anaerobic bacterial fermentation of an acid. In one embodiment, the method comprises at least the step of anaerobically fermenting an acid in the presence of substrate comprising CO, preferably a gaseous substrate comprising CO, wherein the concentration of CO is above a sufficient threshold concentration.

In one embodiment of the invention, ethanol is produced by microbial fermentation of acetic acid/acetate, when the concentration of CO in the fermentation media is above a sufficient threshold concentration. In one embodiment, a substrate comprising CO is provided such that the concentration of CO in a fermentation media is over a threshold concentration of at least about 2.5 mmol/L. In other embodiments, the concentration of CO is over a threshold of at least about 2.75 mmol/L, at least about 3 mmol/L or at least about 3.5 mmol/L.

In one embodiment of the invention, the substrate comprising CO is gaseous and the gaseous substrate is provided such that the CO has a partial pressure at least about 37 psi. In one embodiment, the CO partial pressure is at least about 47 psi.

In another embodiment, there is provided a method of producing alcohols and/or acids, the method including anaerobically fermenting a first substrate in a bioreactor to produce one or more products including alcohols and/or acids; wherein a second substrate comprising CO may be added at a desired time point such that the production of ethanol relative to acetate increases. The second substrate comprising CO is provided such that the concentration of CO exceeds a sufficient threshold concentration. Under such conditions, the alcohol production increases while acid is consumed and CO may be substantially unconverted.

In one embodiment of the invention, the first substrate contains CO; however, the method is not limited to such an embodiment. For example, in some embodiments of the invention, the first substrate may include pyruvate or one or more carbohydrates. The one or more carbohydrates may be, for example and without limitation, cellulose, cellulose hydrolysate, starch, starch hydrolysate, glucose, fructose, xylose, arabinose, or lactose. In one embodiment, the carbohydrate is fructose or xylose. Alternatively, the first substrate may comprise $CO_2$ and/or $H_2$ or any other components suitable for producing acids and/or alcohols by fermentation.

In a further embodiment of the invention, there is provided a method of producing alcohols and/or acids, the method including at least the steps of:
  (a) providing a substrate comprising CO at a first concentration in a bioreactor containing a culture of one or more micro-organisms; and
  (b) anaerobically fermenting the culture to produce one or more products including alcohols and/or acids from said substrate,
wherein the concentration of the substrate provided to the bioreactor may optionally be increased at a desired time point, such that the production of alcohols relative to acids increases.

In one embodiment, the substrate is provided in (a) such that the concentration of CO in the fermentation media is below a sufficient threshold concentration. At such a time that the CO concentration is increased, the substrate may be provided such that the concentration of CO is above a sufficient threshold concentration.

In a further embodiment of the invention, the method includes at least the steps of:
  (a) providing a gaseous substrate comprising CO at a first CO partial pressure in a bioreactor containing a culture of one or more micro-organisms; and
  (b) anaerobically fermenting the culture to produce one or more products including ethanol and/or acetic acid from said substrate,
wherein the CO partial pressure may optionally be increased at a desired time point such that the production of ethanol relative to acetate increases.

In particular embodiments, production of the alcohol and acid and/or microbial growth is monitored throughout during the fermentation process. Under such conditions, the fermentation can readily be changed between substantial acid production to substantial alcohol production, as required or desired. In various embodiments, steps (c) and (d) can be repeated throughout the fermentation process to maintain optimum conditions for alcohol production.

Industrial waste gases comprising CO, such as waste gas form a steel mill can be used to convert acid(s) to alcohol(s) in accordance with the methods of the invention. In addition, CO free gases comprising H2 can also be used to convert acid(s) to alcohol(s) in accordance with the methods of the invention.

The invention also provides a means to alternate between a production phase and a conversion phase by changing CO concentrations to switch from the production phase to the conversion phase and back. For example, and as shown in the examples, increasing the CO concentration above a threshold concentration results in a substantial portion of acetic acid available in a fermentation broth being consumed with a concomitant increase in ethanol production. Reduction of the CO concentration below the threshold concentration may promote microbial growth and acid production as observed in the production phase. For example, a particular fermentation reaction may operate at a desirable CO partial pressure and produce products including acid(s). At a suitable time point, or a particular acid concentration (such as up to 20 g/L, or up to 30 g/L, or up to 40 g/L, or up to 50 g/L), the microbial culture can be perturbed such that the acid(s) is converted to alcohol. In accordance with the methods of the invention, the CO partial pressure can be increased by at least 15 psi, or at least 20 psi, or at least 25 psi, or at least 30 psi, or at least 35 psi, or at least 40 psi such that acid(s) are converted to alcohol(s). Following conversion, the partial pressure can be reduced by at least 15 psi, or at least 20 psi, or at least 25 psi, or at least 30 psi, or at least 35 psi, or at least 40 psi, such that acetate production resumes. This process can be repeated to prevent acetate accumulation and increase alcohol concentration.

In alternative embodiments, the microbial culture may convert acid(s) to alcohol(s) for up to 1 h, or up to 2 h, or up to 3 h, or up to 5 h following perturbation. Subsequently, as the culture adjusts to the elevated CO partial pressure and/or consumes CO such that the CO concentration decreases, the culture will switch back to acid production.

It is contemplated that over several cycles, alcohol levels will increase while acid levels remain at low concentration, such as under 20 g/L, or under 30 g/L, or under 40 g/L, or under 50 g/L).

Two (or More) Bioreactor System

In some embodiments of the invention, the fermentation reactions may be carried out in two or more stages in a system which may comprise a growth (or production) reactor in which the micro-organisms are cultured and optionally acids are produced, and a conversion reactor, to which broth from the growth reactor is fed and a perturbation applied such that acids produced or added are converted to alcohols. As noted above, a pressure rated fermentation bioreactor may be employed.

Referring to FIG. 5, fermentation system 100 comprises a growth bioreactor 1, where fermentation conditions may be adapted to promote microbial biomass accumulation or growth and/or acid production. For example conditions such as liquid nutrient media components, nutrient feed rate, operating pressure, operating pH, substrate content and concentration, substrate feed rate, fermenter agitation rate (if applicable) and cell density may be adapted to promote microbial growth and/or acid production. Exemplary conditions for providing steady state microbial biomass and acid production are provided in the "Examples" section below.

The substrate provided to the growth bioreactor 1 may be selected from those described previously, however, in particular embodiments the substrate is carbohydrate or CO, or is a combination of carbohydrate and CO.

The liquid nutrient medium may be substantially retained in the growth bioreactor 1 for such a time that microbial biomass and/or acids reach desired levels and/or desired production rates. The microbial biomass and/or acid production in the growth bioreactor may be monitored routinely or continuously by means known in the art. Furthermore, conditions in the growth bioreactor may be adjusted to maintain substantially optimum conditions for growth and/or acid production.

It will be appreciated by those skilled in the art that alcohol may also be produced under certain conditions in the growth bioreactor. However, in particular embodiments, acid(s) will be the major product in the growth bioreactor.

At such a time when the desired biomass and/or acid levels or rates have been attained, at least a portion of the acid and optionally at least a portion of the microbial biomass may be passed, by suitable conduit means, from the growth reactor 1 to a conversion reactor 2, continuously or at desired time points. For example at a desired acid concentration in the growth bioreactor 1, such as at least 5 g/L, or at least 10 g/L, or at least 20 g/L, or at least 30 g/L, or at least 40 g/L, or at least 50 g/L, or at least 60 g/L, or at least 70 g/L, or at least 80 g/L, or at least 90 g/L or at least 100 g/L, a portion of the liquid nutrient medium comprising said acids and optionally microbial biomass may be passed to the conversion bioreactor 2, wherein a microbial culture can be perturbed such that acids are converted to alcohols.

The liquid nutrient medium exiting the growth bioreactor 1 will typically be replaced with fresh liquid nutrient medium to provide suitable conditions for steady state biomass and/or acid production. The acid concentration in the growth bioreactor 1 should be maintained below a level at which inhibition of the particular microbe occurs.

In particular embodiments of the invention, a substrate comprising CO is provided to the conversion bioreactor 2 such that the CO concentration in the liquid nutrient medium is at least about 2.5 mmol/L or at least about 2.75 mmol/L, or at least about 3 mmol/L or at least about 3.5 mmol/L. In particular embodiments, the substrate comprising CO is gaseous and may be provided such that the CO partial pressure is at least about 27 psi, or at least about 37 psi or at least about 47 psi.

The acid consumption and/or alcohol production in the conversion bioreactor 2 may be routinely or continuously monitored by means known in the art. At such a time when the liquid nutrient medium reaches a desired alcohol concentration, such as at least 5 g/L, or at least 10 g/L, or at least 20 g/L, or at least 30 g/L, or at least 40 g/L, or at least 50 g/L, or at least 60 g/L, or at least 70 g/L, or at least 80 g/L, or at least 90 g/L or at least 100 g/L, a portion of the liquid nutrient medium comprising said alcohols may be passed to a product recovery apparatus 3. The alcohol concentration in the conversion bioreactor should be maintained below a level at which inhibition of the microbial culture used for alcohol production occurs.

In one embodiment of the invention, the microbe cultured and grown in the growth bioreactor 1 is a carboxydotrophic microbe such as those described hereinbefore, and the conditions are optimised for microbial growth and/or acid production. A second microbe (also a carboxydotrophic microbe) may be provided to the conversion bioreactor 2 and the conditions optimised for alcohol production. The microbial culture provided in the growth and conversion bioreactors may be the same or different. However, in a particular embodiment, the microbe provided to both bioreactors is *Clostridium autoethanogenum*.

In certain embodiments of the invention, the growth bioreactor 1 includes a cell recycle system, wherein at least a portion microbial biomass may be removed from the liquid nutrient medium exiting the growth bioreactor and returned to the growth bioreactor 1. This promotes biomass accumulation in the growth reactor 1. Alternatively, the microbial biomass is not removed from the liquid nutrient medium exiting the growth reactor, but is passed directly into the conversion bioreactor 2.

In particular embodiments, the microbial culture grows and produces acids in the growth reactor 1. At least a portion of the same microbial culture is continuously or intermittently passed to the conversion bioreactor 2, along with acids in the liquid nutrient medium, wherein the conditions in the conversion bioreactor 2 (such as elevated CO concentration) promote the production of alcohol by the same microbial culture.

The retention time of the liquid nutrient medium in the growth bioreactor 1 may be regulated to optimise biomass accumulation and/or acid production. For example, at start up, biomass accumulation may be desirable and the flow rate of liquid nutrient media passing into and out of the growth bioreactor 1 may be reduced to increase the retention time of the media in the growth bioreactor 1 and thus allow biomass and/or acid to reach desired levels or rates.

When the biomass and/or acid production approaches or reaches desired levels or rates, the liquid retention time may be reduced by increasing the flow rate of the liquid nutrient medium from the growth bioreactor 1 to the conversion bioreactor 2. In certain embodiments, the microbial biomass and/or acid levels are monitored and the retention time may be adjusted to achieve a substantially steady state acid concentration. Furthermore, conditions may also be regulated to achieve the desired steady state acid concentration of at least 5 g/L, or at least 10 g/L, or at least 20 g/L, or at least 30 g/L, or at least 40 g/L, or at least 50 g/L, or at least 60 g/L, or at least 70 g/L, or at least 80 g/L, or at least 90 g/L or at least 100 g/L, in the growth bioreactor 1.

The liquid retention time of the liquid nutrient media can also be regulated in the conversion bioreactor 2 to achieve efficient alcohol production. For example, the liquid nutrient media may be provided continuously at a constant rate and the volume of the liquid nutrient medium in the conversion bioreactor 2 may be adjusted to provide a retention time suitable to achieve desirable alcohol conversion. In particular embodiments of the invention, the rate of alcohol production in the alcohol conversion phase at elevated CO concentrations is faster than the rate of growth and/or acid production. As such, the conversion bioreactor 2 may be substantially smaller than the growth bioreactor 1 leading to substantially lower liquid retention time in the conversion bioreactor 2.

Upon consideration of the instant disclosure, those skilled in the art will appreciate suitable or desirable configurations for each bioreactor, however in a particular embodiment, a portion of the liquid nutrient medium comprising a microbial culture, acid and optionally alcohol is passed to a second vessel configured as a plug flow bioreactor. The CO partial pressure can be elevated in the plug flow vessel, such that as a portion of the liquid nutrient medium passes through acid(s) are converted to alcohol(s). Those skilled in the art will appreciate means for maintaining flow through the bioreactor, such as static mixers. Furthermore, the bioreactor may include additional substrate delivery means throughout in order to maintain the required and/or desired CO concentration throughout the bioreactor.

In another embodiment, the production bioreactor comprises at least one microbial culture and the conversion bioreactor comprises at least one microbial culture. While fermentation broth containing acid(s) and/or alcohol(s) can pass from the production bioreactor to the conversion reactor and from the conversion bioreactor to product recovery, the respective microbial cultures are substantially retained in each bioreactor by cell recycle systems. In such embodiments, the microbial cultures may be different, provided the culture in the production bioreactor produces acid(s) and the culture in the conversion bioreactor converts acid(s) to alcohol(s). In a particular embodiments, the microbial culture in the conversion bioreactor converts acid(s) to alcohol(s) at elevated CO partial pressure.

In certain embodiments, acid(s) produced from other fermentation and/or industrial processes can be added to the conversion bioreactor as desired to convert to alcohol(s).

In another embodiment of the invention, a fermentation system comprising multiple growth bioreactors, configured to supply a single conversion bioreactor, with liquid nutrient media comprising acids and optionally microbial biomass is provided. For example, referring to FIG. 6, fermentation system 101 comprises a first and second growth bioreactor 1a and 1b, and each may be configured to produce acid(s). Liquid nutrient medium containing acids and optionally biomass from the growth bioreactors 1a and b, may be fed into the conversion bioreactor 2 for alcohol production. Alternatively, a first growth bioreactor 1a may be configured for rapid biomass accumulation (for example high liquid retention time), while the second growth bioreactor 1b is configured for optimal acid production (for example lower liquid retention time). The liquid retention times of each growth bioreactor 1a and b, can be adjusted accordingly to maintain optimum alcohol producing conditions throughout the whole system.

In embodiments including multiple growth bioreactors, one or more growth bioreactors may be entirely shut down for a period (such as for maintenance), without substantially adversely affecting alcohol production.

EXAMPLES

Preparation of Media

| Media Component | Concentration per 1.0 L of Media (LM23) | Concentration per 1.0 L of Media (LM33) |
| --- | --- | --- |
| $MgCl_2 \cdot 6H_2O$ | 0.5 g | 0.5 g |
| NaCl | 0.2 g | 0.2 g |
| $CaCl_2$ | 0.2 g | 0.2 g |
| 100 mM sodium phosphate buffer (pH 6.0)* | 160 ml | — |
| $NaH_2PO_4$ | — | 2.04 g |
| $NH_4Cl$ | 0.6 g | 2.5 g |
| 85% $H_3PO_4$ | 0.05 ml | — |
| KCl | 0.15 g | 0.15 g |
| Composite trace metal solution (LSO6) | 10 mL | 10 mL |
| Composite B vitamin Solution (LS03) | 10 mL | 10 mL |
| Resazurin (1000 mg/L stock) | 1 mL | 2 mL |
| $FeCl_3$ | 0.0025 g | 0.01 g |
| Cysteine HCl monohydrate | 0.75 g | 0.5 g |
| Agarose (optional) | 15 g | 15 g |
| Distilled water | To 1 litre | To 1 litre |

*Combine $NaH_2PO_4$ (13.2 g) and $Na_2HPO_2 \cdot 7H_2O$ (1.1 g) in $H_2O$ (1 L).

| Composite B vitamin Solution (LS03) | per L of Stock | Composite trace metal solution (LSO6) | per L of stock |
| --- | --- | --- | --- |
| Biotin | 20.0 mg | Nitrilotriacetic Acid | 1.5 g |
| Folic acid | 20.0 mg | $MgSO_4 \cdot 7H_2O$ | 3.0 g |

-continued

| Composite B vitamin Solution (LS03) | per L of Stock | Composite trace metal solution (LSO6) | per L of stock |
|---|---|---|---|
| Pyridoxine hydrochloride | 10.0 mg | $MnSO_4 \cdot H_2O$ | 0.5 g |
| Thiamine·HCl | 50.0 mg | NaCl | 1.0 g |
| Riboflavin | 50.0 mg | $FeSO_4 \cdot 7H_2O$ | 0.1 g |
| Nicotinic acid | 50.0 mg | $Fe(SO_4)_2(NH_4)_2 \cdot 6H_2O$ | 0.8 g |
| Calcium D-(*)-pantothenate | 50.0 mg | $CoCl_2 \cdot 6H_2O$ | 0.2 g |
| Vitamin B12 | 50.0 mg | $ZnSO_4 \cdot 7H_2O$ | 0.2 g |
| p-Aminobenzoic acid | 50.0 mg | $CuCl_2 \cdot 2H_2O$ | 0.02 g |
| Thioctic acid | 50.0 mg | $AlK(SO_4)_2 \cdot 12H_2O$ | 0.02 g |
| Distilled water | To 1 Litre | $H_3BO_3$ | 0.30 g |
| | | $NaMoO_4 \cdot 2H_2O$ | 0.03 g |
| | | $Na_2SeO_3$ | 0.02 g |
| | | $NiCl_2 \cdot 6H_2O$ | 0.02 g |
| | | $Na_2WO_4 \cdot 6H_2O$ | 0.02 g |
| | | Distilled water | To 1 Litre |

Media was prepared at pH 5.5 as follows. All ingredients with the exception of Cysteine-HCl were mixed in 400 ml distilled water. This solution was made anaerobic by heating to boiling and allowing it to cool to room temperature under a constant flow of 95% CO, 5% CO2 gas. Once cool, the Cysteine-HCl was added and the pH of the solution adjusted to 5.5 before making the volume up to 1000 ml; anaerobicity was maintained throughout the experiments.

Bacteria:

*Clostridium autoethanogenum* were obtained from the German Resource Centre for Biological Material (DSMZ). The accession number given to the bacteria is DSMZ 10061. Alternatively, the *Clostridium autoethanogenum* used is that deposited at the German Resource Centre for Biological Material (DSMZ) and allocated the accession number 19630.

Continuous Fermentation in Continuous Stirred Tank Reactor (CSTR) (Typical Set-Up):

A five-liter bioreactor was charged with 4.9 L of LM23 or LM33 media prepared as described above. The gas was switched to 95% CO, 5% $CO_2$ at atmospheric pressure prior to inoculation with 100 ml of a *Clostridium autoethanogenum* culture. The bioreactor was maintained at 37° C. stirred at 200 rpm at the start of the culture. During the growth phase, the agitation was increased to 400 rpm. The pH was adjusted to 5.5 and maintained by automatic addition of 5 M NaOH. Fresh anaerobic media was continuously added into the bioreactor to maintain a defined biomass and acetate level the bioreactor.

Batch Fermentation Under Pressure in Serum Bottle

Sterile serum bottles were purged three times with CO containing gas (see examples for composition) and then evacuated to a vacuum of −5 psi. 50 ml of active culture containing biomass, acetate and traces of ethanol under atmospheric pressure was transferred directly from a continuous bioreactor into the 234 ml serum bottle. The 204 ml headspace was then filled with CO containing gas to the required overpressure. A shaking incubator was used and the reaction temperature was maintained at 37° C.

Cell Density:

To determine the cell density in these experiments, the absorbance of the samples was measured at 600 nm (spectrophotometer) and the dry mass determined via calculation according to published procedures. The level of metabolites was characterized using High Performance Liquid Chromatography (HPLC) and in some cases Gas Chromatography (GC).

HPLC:

HPLC System Agilent 1100 Series. Mobile Phase: 0.0025N Sulphuric Acid. Flow and pressure: 0.800 mL/min. Column: Alltech IOA; Catalog #9648, 150×6.5 mm, particle size 5 µm. Temperature of column: 60° C. Detector: Refractive Index. Temperature of detector: 45° C.

Method for Sample Preparation:

400 µL of sample and 50 µL of 0.15M $ZnSO_4$ and 50 µL of 0.15M $Ba(OH)_2$ are loaded into an Eppendorf tube. The tubes are centrifuged for 10 min. at 12,000 rpm, 4° C. 200 µL of the supernatant are transferred into an HPLC vial, and 5 µl are injected into the HPLC instrument.

Gas Chromatography:

Gas Chromatograph HP 5890 series II utilizing a Flame Ionization Detector. Capillary GC Column: EC1000-Alltech EC1000 30 m×0.25 mm×0.25 um. The Gas Chromatograph was operated in Split mode with a total flow of hydrogen of 50 mL/min with 5 mL purge flow (1:10 split), a column head pressure of 10 PIS resulting in a linear velocity of 45 cm/sec. The temperature program was initiated at 60° C., held for 1 minute then ramped to 215° C. at 30° C. per minute, then held for 2 minutes. Injector temperature was 210° C. and the detector temperature was 225° C.

Method for Sample Preparation:

500 µL sample is centrifuged for 10 min at 12,000 rpm, 4° C. 100 µL of the supernatant is transferred into an GC vial containing 200 µL water and 100 µL of internal standard spiking solution (10 g/L propan-1-ol, 5 g/L iso-butyric acid, 135 mM hydrochloric acid). 1 µL of the solution is injected into the GC instrument.

Example 1

Conversion of Organic Acid to Corresponding Alcohol

Example 1A

Conversion of Butyric Acid to Butanol in a CSTR

An eight-liter reactor was filled with 7200 ml of the media LM23 and autoclaved for 30 minutes at 121° C. While cooling down, the media was sparged with N2. The gas was switched to 95% CO, 5% CO2 prior inoculation with 160 ml of a *Clostridium autoethanogenum* culture. The bioreactor was maintained at 37° C. stirred at 200 rpm at the start of the culture. During the growth phase, the agitation was increased to 500 rpm. The pH was set to 5.5 and maintained by automatic addition of 5 M NaOH. The n-butyrate solution containing 20 g butyric acid buffered to pH 5.5 was added directly into the actively growing culture. Samples of the fermentation broth were taken at 0, 24 and 48 hours after butyric acid addition (see Table 1).

TABLE 1

Conversion of 20 g of n-Butyrate into 1-Butanol by an 8 litre culture of *C. autoethanogenum* producing acetate and ethanol in a bioreactor maintained at pH 5.5.

| Time [h] | 0 | 24 | 48 |
|---|---|---|---|
| Butanol produced [g] | 0.0 | 4.0 | 8.2 |

Starting conditions: active culture of *C. autoethanogenum*, producing acetate (8.3 g/l) and ethanol (5.4 g/l) pH 5.5 and sparging gas containing 95% CO in CO2.

Example 18

Conversion of Acetate and Butyrate to Corresponding Alcohols

Serum vials were prepared in accordance with the above. Once microbial growth was established (associated with acetate and small amounts of ethanol produced), the following compounds were added into the 50 ml active culture in the serum bottle: 1 ml of Sodium Dithionite 10 g/l solution, 2 ml of n-butyric acid solution 100 g/l (pH adjusted to 5.5 with Sodium Hydroxide 5 M). The gas phase was exchanged for 25 psig overpressure of a mixture of 95% CO, 5% $CO_2$ gas. After addition of the acid, 1 ml sample was taken for quantification of the metabolites at various time points (see Table 2).

TABLE 2

Conversion of n-butyrate into 1-Butanol by a culture of *C. autoethanogenum* producing acetate and ethanol in a serum bottle at pH 5.5 in presence or absence of 0.8 mM methylviologen (MV).

| Time (h) | Methyl-viologen conc (mM) | Acetate conc (g/L) | Ethanol conc (g/L) | Butyrate conc (g/L) | Butanol conc (g/L) |
|---|---|---|---|---|---|
| 0 | 0 | 4.50 | 1.26 | 4.19 | 0.00 |
| 2 | 0 | 5.00 | 1.40 | 3.93 | 0.16 |
| 4 | 0 | 4.19 | 1.28 | 3.68 | 0.30 |
| 22 | 0 | 4.61 | 1.44 | 3.81 | 0.41 |
| 0 | 0.8 | 4.72 | 1.24 | 3.81 | 0.00 |
| 2 | 0.8 | 4.87 | 1.42 | 3.66 | 0.17 |
| 4 | 0.8 | 4.88 | 1.49 | 3.42 | 0.34 |
| 22 | 0.8 | 4.15 | 1.84 | 2.27 | 1.35 |

Starting conditions: active culture of *C. autoethanogenum*, producing acetate (4.7 g/l) and ethanol (1.2 g/l) pH 5.5, headspace: 25 psig overpressure of 95% CO in CO2.

The presence of the mediator methyl viologen significantly inhibits conversion of n-butyrate to n-butanol (Table 2). Furthermore, butyric acid was stoichiometrically converted to butanol (FIG. 1).

The results illustrate a number of significant advantages over previously reported methods for the microbial conversion of acids to their corresponding alcohols. For example, they demonstrate for the first time that *Clostridium autoethanogenum* (C. auto) can be used to produce alcohols which it is not known to be able to produce under standard fermentation conditions.

The bacterial cells do not need to be harvested prior to addition of acid to produce a desired alcohol; the conversion of acid to alcohol is carried out directly in the culture media. This significantly reduces handling of cells, the risk of cell damage which may be caused by centrifugation and resuspension, and the risk of oxygen contamination.

The conversion does not require the use of a mediator, such as methyl viologen. In fact, the addition of methyl viologen was demonstrated to inhibit or at least reduce the rate of conversion of acids to alcohols. Such mediators are often toxic. Removing the need for a mediator has the advantage of reducing handling of toxic chemicals and reducing the costs associated with production of alcohols.

At least in the case of *C. autoethanogenum*, the bacterial cells can be maintained at the same pH and temperature during the growth phase and the acid to alcohol conversion phase (37° C. and pH 5.5). This simplifies the process and reduces the risk of shock to the cells.

Further, the addition of the acid when the bacteria are in the conversion phase, and the ability of the cells to continue to consume carbon monoxide and produce acetate and ethanol (for example) while they are converting the added acids to corresponding alcohols, provides a method in which a number of valuable products can be produced simultaneously.

Example 1C

Conversion of Various Acids to Corresponding Alcohols

Serum vials were prepared in accordance with the above. However, 5 mL of an aqueous acid solution was added to the empty vial and the pH adjusted to 5.5 with NaOH. Sodium dithionate (0.5 mL of a 10 g/L aqueous solution) or cysteine (1 mL of a 6.25 g/L aqueous solution) was added prior to inoculation. Each serum vial was pressurised to 30 psig with 95% CO gas and incubated at 37° C. with constant shaking. Samples of the fermentation broth were taken at 72 h (see Table 3).

TABLE 3 conversion of various acids to corresponding alcohols by *Clostridium autoethanogenum*.

| Reducing agent | Acid | Initial acid concentration (g/L) | Alcohol concentration at 72 h (g/L) |
|---|---|---|---|
| Sodium dithionite | Propionic | 0.9 | 0.14 (propanol) |
| Sodium dithionite | Propionic | 1.4 | 0.38 (propanol) |
| Sodium dithionite | Butyric | 2.3 | 0.17 (butanol) |
| Sodium dithionite | Butyric | 3.1 | 0.52 (butanol) |
| Sodium dithionite | Valeric | 1.0 | 0.14 (pentanol) |
| Sodium dithionite | Valeric | 1.7 | 0.24 (pentanol) |
| Sodium dithionite | Hexanoic | 0.9 | 0.06 (hexanol) |
| Sodium dithionite | Hexanoic | 1.7 | 0.09 (hexanol) |
| Cysteine | Isovaleric | 1.41 | 0.03 (3-methylbutanol) |
| Cysteine | 2-methyl-butyric | 1.87 | 0.06 (2-methylbutanol) |

As can be seen above, *Clostridium autoethanogenum* can be used to convert a variety of acids to their corresponding alcohols in the presence of a reducing agent. Again, this is particularly significant, as the above acids and alcohols are not known to be naturally produced metabolites of C. auto.

Example 2

Effect of Reducing Agent Concentration on Alcohol Production

Example 2A

Effect of Sodium Dithionite Concentration on Alcohol Production

Serum vials were prepared in accordance with the above. However, sodium dithionate (10 g/L aqueous solution) was added prior to inoculation. Each serum vial was pressurised to 30 psig with 70% CO 15% $CO_2$, 14% $N_2$, 1% $H_2$ gas and incubated at 37° C. with constant shaking. Samples of the fermentation broth were taken at 48 h (see Table 4)

TABLE 4 conversion of acetate to ethanol at different sodium dithionite concentrations by *Clostridium autoethanogenum*.

| Sodium dithionite conc (g/L) | Final Acetate conc (g/L) | Final Ethanol conc (g/L) |
|---|---|---|
| 0 | 12.2 | 0.5 |
| 0.1 | 10.9 | 0.6 |

TABLE 4-continued conversion of acetate to ethanol at different sodium dithionite
concentrations by *Clostridium autoethanogenum*.

| Sodium dithionite conc (g/L) | Final Acetate conc (g/L) | Final Ethanol conc (g/L) |
|---|---|---|
| 0.15 | 10.1 | 1.0 |
| 0.2 | 9.6 | 1.9 |
| 0.3 | 10.2 | 1.4 |
| 0.4 | 10.2 | 1.0 |
| 0.5 | 10.2 | 1.0 |

The results signify that while acid to alcohol conversion occurs over a wide range of reducing agent concentrations, there is an optimum concentration of approximately 2 g/L.

Example 28

Effect of Sodium Sulfide Concentration on Alcohol Production

Sterile 234 ml serum bottles were purged with 100% N2 gas and then 50 ml of media (LM33) according to above recipe were added and then autoclaved at 121° C. for 20 minutes. The media was reduced with Cr(II) solution (approx 0.4 mM) and sodium sulfide aqueous solution added. The serum bottles were inoculated with 2.5 ml of an actively growing *Clostridium autoethanogenum* culture from a continuous bioreactor. The 184 ml headspace was purged three times with 70% CO, 1% H2, 15% CO2, and 14% N2 gas and evacuated to a vacuum of −14 psig to remove the N2 background and was then filled with 70% CO, 1% H2, 15% CO2, and 14% N2 gas to 30 psig. The reaction temperature was maintained at 37° C. Samples were taken at intervals and the headspace was purged and refreshed up to 30 psi following sampling (see Table 5).

Example 3

Effect of CO Partial Pressure

Example 3A

Effect of the CO Partial Pressure on Alcohol Production

Serum vials were prepared in accordance with the above. Each serum vial was pressurised to 30 or 40 or 50 psia using a 95% CO in CO2 gas mixture and incubated at 37° C. with constant shaking. Samples of the fermentation broth were taken at 18 h (see Table 6)

TABLE 6

Effect of different headspace overpressures on the metabolism of a gaseous substrate comprising 95% CO in $CO_2$ by a culture of *C. autoethanogenum* in a serum bottle at pH 5.5 after 18 hours of fermentation.

| Start Overpressure | 30 psia | 40 psia | 50 psia |
|---|---|---|---|
| Acetate (g/l) | 5.4 | 5.7 | 0.2 |
| Ethanol (g/l) | 0.5 | 0.8 | 2.6 |
| Final Overpressure (psig) | 2 | 8 | 29 |
| Pressure drop (psi) | 13 | 17 | 6 |

Starting conditions: continuous culture of *C. autoethanogenum*, containing 3.3 g/l acetate and 0.0 g/l ethanol at pH 5.5.

In the bioreactor bottles at 30 psi to 40 psi, about 2 g/l acetate and 0.6 g/l ethanol were produced and the pressure drop in the headspace was about 17 psi. This indicates that a substantial amount of the CO has been used for acetate production.

Surprisingly, at 50 psi, about 3 g/l acetate was consumed and 2.6 g/l ethanol produced. The results indicate that there is

TABLE 5 conversion of acetate to ethanol at different sodium sulfide
concentrations by *Clostridium autoethanogenum*.

| | 10 mM Na2S | | 6 mM Na2S | | 3 mM Na2S | | 1 mM Na2S | | 0 mM Na2S | |
|---|---|---|---|---|---|---|---|---|---|---|
| Time (h) | Acet. (g/L) | EtOH (g/L) | Acet. (g/L) | EtOH (g/L) | Acet. (g/L) | EtOH (g/L) | Acet. (g/L) | EtOH (g/L) | Acet. (g/L) | EtOH (g/L) |
| 5 | 0.46 | 0 | 0.40 | 0 | 0.41 | 0 | 0.45 | 0 | 0.44 | 0 |
| 23 | 0.50 | 0.09 | 0.49 | 0 | 0.45 | 0 | 0.42 | 0 | 0.89 | 0 |
| 30 | 0.50 | 0 | 0.54 | 0 | 0.49 | 0 | 0.42 | 0 | 1.12 | 0 |
| 52 | 0.51 | 0 | 0.49 | 0.20 | 0.72 | 0 | 0.42 | 0 | 2.90 | 0 |
| 77 | 0.47 | 0.19 | 0.35 | 0.37 | 0.60 | 0.22 | 0.50 | 0.11 | 4.12 | 0 |
| 95 | 0.39 | 0.29 | 0.25 | 0.47 | 0.56 | 0.30 | 0.31 | 0.40 | 4.15 | 0 |
| 102 | 0.35 | 0.31 | 0.23 | 0.5 | 0.54 | 0.30 | 0.30 | 0.42 | 4.17 | 0 |
| 118 | 0.33 | 0.37 | 0.18 | 0.56 | 0.52 | 0.31 | 0.20 | 0.50 | 4.20 | 0 |
| 126 | 0.33 | 0.4 | 0.18 | 0.58 | 0.53 | 0.35 | 0.20 | 0.55 | 4.17 | 0 |
| 143 | 0.31 | 0.48 | 0.18 | 0.64 | 0.50 | 0.40 | 0.13 | 0.63 | | |
| 166 | 0.24 | 0.57 | 0.15 | 0.66 | 0.42 | 0.51 | 0.14 | 0.66 | | |

Note:
serum vials with various sodium sulfide concentrations were run in duplicate and averages are provided.

The results indicate that while there is a short lag phase associated with a small increase in acetate concentration, the acetate in each of the vials containing sodium sulfide is converted into alcohols over the time course of the experiment.

an optimum threshold CO partial pressure at which acetate to alcohol conversion occurs for an extended period. As CO concentration is proportional to CO partial pressure, the results indicate there is a sufficient CO concentration threshold at which C. auto converts acids to alcohols. However, it should be noted that lower pressure systems may also convert acids to alcohol, but as CO becomes depleted acetate production prevails. Additionally, under particularly CO (or H2) depleted conditions, the culture may reconsume alcohol to produce acetate (see example 4).

Example 3B

Effect of CO Partial Pressure on Alcohol Production

Based on these results, a similar fermentation was conducted using the same gaseous substrate with media supplemented with different carbon sources. Serum vials were prepared in accordance with the above. Each serum vial was pressurised to 40 or 50 psia using a 95% CO in CO2 gas mixture and incubated at 37° C. with constant shaking. A control bioreactor bottle (A) was unsupplemented, while other bottles were supplemented with some fructose (B), xylose (C) or pyruvate (D). These bottles were incubated at 37° C. with constant agitation. The metabolites and biomass concentrations, as well as the headspace overpressure and pH, were measured at the start of the fermentation and after 40 hours. Results at 40 psia are shown in Table 7 and results at 50 psia are shown in Table 8.

TABLE 7

Metabolism of 40 psia overpressure of a gaseous substrate comprising 95% CO in $CO_2$ by a culture of *C. autoethanogenum* in a serum bottle at pH 5.5 after 40 h of fermentation.

| A | Acetate | Ethanol | Biomass | Overpressure | pH | Supplement |
|---|---------|---------|---------|--------------|-----|------------|
| Start | 6.3 | 0.4 | 0.7 | 25 | 5.5 | — |
| End | 10.0 | 1.0 | 0.7 | 7 | 4.6 | — |
| Difference | +3.7 | +0.6 | +0.0 | −18 | −0.9 | — |

| B | Acetate | Ethanol | Biomass | Overpressure | pH | Fructose |
|---|---------|---------|---------|--------------|-----|----------|
| Start | 6.3 | 0.5 | 0.7 | 25 | 5.5 | 0.9 |
| End | 10.1 | 1.7 | 0.7 | 9 | 4.6 | 0.0 |
| Difference | +3.8 | +1.2 | +0.0 | −16 | −0.9 | −0.9 |

| C | Acetate | Ethanol | Biomass | Overpressure | pH | Xylose |
|---|---------|---------|---------|--------------|-----|--------|
| Start | 6.1 | 0.4 | 0.7 | 25 | 5.5 | 0.8 |
| End | 9.8 | 1.4 | 0.9 | 7 | 4.6 | 0.1 |
| Difference | +3.7 | +1.0 | +0.2 | −18 | −0.9 | −0.7 |

| D | Acetate | Ethanol | Biomass | Overpressure | pH | Pyruvate |
|---|---------|---------|---------|--------------|-----|----------|
| Start | 7.0 | 0.0 | 0.8 | 25 | 5.5 | 0.8 |
| End | 10.1 | 0.8 | 0.7 | 8 | 4.8 | 0.0 |
| Difference | +3.1 | +0.8 | −0.1 | −17 | −0.7 | −0.8 |

Starting conditions: continuous culture of *C. autoethanogenum* at dilution rate = $0.04\ h^{-1}$, continuous flow of gaseous substrate comprising 95% CO in $CO_2$ (no overpressure), producing acetate and ethanol at pH 5.5. Data for acetate, ethanol, fructose, xylose, pyruvate are concentrations in gram per litre. Biomass is given as gram of cell dry weight per litre. Overpressure of gas in the headspace is shown in psig.

In all the bioreactor bottles at 40 psia, for all conditions tested here, about 3.5 g/l acetate and minor amounts of ethanol were produced. The pressure drop in the headspace was about 17 psig. This indicates that a substantial portion of the CO has been consumed for acetate production. The pH decreased by about 0.9 units to 4.6. In all cases, there was minimal microbial growth.

TABLE 8

Metabolism of 50 psia overpressure of a gaseous substrate comprising 95% CO in $CO_2$ by a culture of *C. autoethanogenum* in a serum bottle at pH 5.5 after 40 h of fermentation.

| A | Acetate | Ethanol | Biomass | Overpressure | pH | Supplement |
|---|---------|---------|---------|--------------|-----|------------|
| Start | 6.3 | 0.4 | 0.7 | 35 | 5.5 | — |
| End | 1.1 | 4.3 | 0.4 | 25 | 6.4 | — |
| Difference | −5.2 | +3.9 | −0.3 | −10 | +0.9 | — |

| B | Acetate | Ethanol | Biomass | Overpressure | pH | Fructose |
|---|---------|---------|---------|--------------|-----|----------|
| Start | 6.3 | 0.5 | 0.7 | 35 | 5.5 | 0.9 |
| End | 1.9 | 3.9 | 0.4 | 28 | 6.4 | 0.0 |
| Difference | −4.4 | +3.4 | −0.3 | −7 | +0.9 | −0.9 |

TABLE 8-continued

Metabolism of 50 psia overpressure of a gaseous substrate comprising 95% CO in $CO_2$ by a culture of *C. autoethanogenum* in a serum bottle at pH 5.5 after 40 h of fermentation.

| C | Acetate | Ethanol | Biomass | Overpressure | pH | Xylose |
|---|---|---|---|---|---|---|
| Start | 6.1 | 0.4 | 0.7 | 35 | 5.5 | 0.8 |
| End | 2.8 | 3.4 | 0.4 | 30 | 6.4 | 0.0 |
| Difference | −3.3 | +3.0 | −0.3 | −5 | +0.9 | −0.8 |

| D | Acetate | Ethanol | Biomass | Overpressure | pH | Pyruvate |
|---|---|---|---|---|---|---|
| Start | 7.0 | 0.0 | 0.8 | 35 | 5.5 | 0.8 |
| End | 1.5 | 4.5 | 0.4 | 26 | 6.5 | 0.0 |
| Difference | −5.5 | +4.5 | −0.4 | −9 | +1.0 | −0.8 |

Starting conditions: continuous culture of *C. autoethanogenum* at dilution rate = 0.04 h$^{-1}$, continuous flow of gaseous substrate comprising 95% CO in $CO_2$ (no overpressure), producing acetate and ethanol at pH 5.5. Data for acetate, ethanol, fructose, xylose, pyruvate are concentrations in gram per litre. Biomass is given as gram of cell dry weight per litre. Overpressure of gas in the headspace is shown in psig.

In all the bioreactor bottles at 50 psia, for all conditions tested here, significant amounts of acetate were consumed, and more than 3 g/l ethanol was produced. There is a strong correlation between acetate consumption and ethanol production. Acetate consumption/ethanol production occurs in such a way that for each mole of acetate consumed approximately one mole of ethanol was produced (Table 9). However, the supplemented carbohydrate (or pyruvate) was substantially consumed, and the biomass levels, estimated by optical density, decreased. In each instance, the pressure drop in the headspace was below 10 psi. In all cases, the pH increased by about 0.9 units to 6.4.

TABLE 9

Molar ratios for batch fermentation at 35 psi overpressure, based on results shown in Table 2 and 3.

| | Gas only | Gas and fructose | Gas and xylose | Gas and pyruvate |
|---|---|---|---|---|
| 1. Acetate consumed/Acetate at start | 0.83 | 0.70 | 0.54 | 0.79 |
| 2. Ethanol produced/Acetate at start | 0.81 | 0.70 | 0.64 | 0.84 |
| 3. Ethanol produced/Acetate consumed | 0.98 | 1.01 | 1.19 | 1.07 |

Given the acetate consumed/acetate at start (row 1), at least 50% and in some cases over 75% of the acetate present in the fermentation broth is consumed at elevated pressure. Given the ethanol produced/acetate at start (row 2), at least 60% and in some cases at least 80% of the consumed acid is replaced by alcohol. Given ethanol produced/acetate consumed (row 3), there is a strong correlation between the amount of acetate consumed in the fermentation process, and the alcohol produced. The theoretical level of dissolved CO in the media at 40 and 50 psia headspace overpressure was calculated in Table 10 based on the Henry's law.

TABLE 10

Calculation of the dissolved CO concentration in media at different headspace overpressure of a gaseous substrate comprising 95% CO in $CO_2$.

| Overpressure in headspace | psia | 40 | 50 |
|---|---|---|---|
| Partial pressure of CO in headspace | psi | 37.7 | 47.2 |
| Dissolved CO concentration in media | mmol/l | 2.43 | 3.05 |

Henry's constant for CO in water at 298 K is 1052.6 L · atm · mol$^{-1}$

The results presented here demonstrate that there is a CO partial pressure above which the metabolism of *C. autoethanogenum* changes substantially from production of acetate and biomass from the CO substrate to the conversion of at least a portion of acetate into ethanol. Thus, for a CO partial pressure below 37 psi, acetate and biomass are the major products of CO gas metabolism and pH becomes acidic, and further growth is inhibited. When the CO partial pressure is above 37 psi, biomass growth and acetate production appears to be inhibited, and consumption of acetate occurs. Furthermore, ethanol production occurs with minor CO consumption. At the same time, pH increases until it reaches 6.5, where the bacteria appear to be substantially inhibited and the conversion of acetate to ethanol stops. There is no noticeable effect of fructose, xylose or pyruvate at the concentration tested.

Example 3C

Effect of CO Partial Pressure on Alcohol Production

Serum vials were prepared in accordance with the above. Each serum vial was pressurised to 25 psig (40 psia) with the indicated gas and incubated at 37° C. with constant shaking. Samples of the fermentation broth were taken at intervals of 1 h, 3 h and 5 h (see Table 11).

TABLE 11 conversion of acetate to alcohol at various CO partial pressures by *Clostridium autoethanogenum* over 5 hours.

| Gas composition | Time | Acetate conc (g/L) | Ethanol conc (g/L) | Pressure (psig) |
|---|---|---|---|---|
| 100% CO | 0 | 11.914 | 0 | 25 |
| | 1 | 11.273 | 0.523 | 25.1 |
| | 3 | 10.488 | 1.295 | 22.7 |
| | 5 | 10.337 | 1.518 | 21.4 |

TABLE 11-continued conversion of acetate to alcohol at various CO partial pressures by *Clostridium autoethanogenum* over 5 hours.

| Gas composition | Time | Acetate conc (g/L) | Ethanol conc (g/L) | Pressure (psig) |
|---|---|---|---|---|
| 90% CO; 10% N2 | 0 | 11.914 | 0 | 25 |
|  | 1 | 11.177 | 0.548 | 23.3 |
|  | 3 | 10.407 | 1.315 | 21.2 |
|  | 5 | 10.12 | 1.602 | 19.5 |
| 80% CO; 20% N2 | 0 | 11.914 | 0 | 25 |
|  | 1 | 11.389 | 0.44 | 23.9 |
|  | 3 | 11.042 | 1.055 | 22.5 |
|  | 5 | 10.605 | 1.267 | 21.3 |
| 70% CO; 30% N2 | 0 | 11.914 | 0 | 25 |
|  | 1 | 11.341 | 0.538 | 25.8 |
|  | 3 | 10.51 | 1.193 | 23.4 |
|  | 5 | 10.579 | 1.445 | 21.8 |
| 60% CO; 40% N2 | 0 | 11.914 | 0 | 25 |
|  | 1 | 11.311 | 0.565 | 26.3 |
|  | 3 | 10.959 | 1.297 | 23.5 |
|  | 5 | 10.493 | 1.5 | 21.6 |
| 50% CO; 50% N2 | 0 | 11.9 | 0 | 25 |
|  | 1 | 11.3 | 0.533 | 25.9 |
|  | 3 | 11.0 | 1.236 | 23.5 |
|  | 5 | 10.5 | 1.448 | 21.9 |

The results indicate that the sufficient threshold CO partial pressure at which acids are converted to alcohols is less than 20 psia. Over a short reaction time scale (c.f. examples 3A-C), acetate is converted to alcohol substantially stoichiometrically at all CO partial pressures tested. Accordingly, a CO partial pressure over 20 psia is sufficient for C. auto to convert acids to alcohols.

Example 4

Effect of Gas Composition

Example 4A

Effect of Pure Gas on Acetate Conversion to Ethanol

Serum vials were prepared in accordance with the above. Each serum vial was pressurised to 25 psig (40 psia) with the indicated gas and incubated at 37° C. with constant shaking. Samples of the fermentation broth were taken at intervals of 1 h, 3 h and 5 h (see table 12).

TABLE 12

Conversion of acetate to ethanol by *Clostridium autoethanogenum* using alternative gas compositions.

| Gas composition | Time | Acetate conc (g/L) | Ethanol conc (g/L) | Pressure (psig) |
|---|---|---|---|---|
| 100% N2 | 0 | 12.531 | 0.133 | 26.1 |
|  | 1 | 12.742 | 0 | 27.5 |
|  | 3 | 12.394 | 0 | 27.1 |
|  | 5 | 12.551 | 0 | 26.6 |
| 100% H2 | 0 | 12.531 | 0.133 | 25.8 |
|  | 1 | 11.921 | 0.384 | 24.8 |
|  | 3 | 11.811 | 0.527 | 23.3 |
|  | 5 | 11.998 | 0.546 | 22.5 |
| Steel Mill Waste Gas (approx 53% CO; 18% CO2; 26% N2; 3% H2) | 0 | 12.531 | 0.133 | 24.8 |
|  | 1 | 11.256 | 1.007 | 23.6 |
|  | 3 | 10.668 | 1.605 | 20.6 |
|  | 5 | 11.688 | 1.362 | 16.7 |

The results clearly indicate a reducing gas, such as CO or H2 is necessary in order for C. auto to convert acids to alcohols. It is considered that hydrogen can be used in place of CO as the metabolic pathway from acids to alcohols includes hydrogenase enzymes. It is further considered that while H2 is a suitable energy source for converting acids to alcohols it would not be adequate for biosynthesis and/or acetate production, which requires a carbon source as well as an energy source.

Example 48

Effect of Gas Composition on Ethanol Production

Serum vials were prepared in accordance with the above. However, prior to inoculation, the vials were spiked with butyric acid solution buffered to pH 5.5 with NaOH(aq). Initial concentrations at t=0 were acetate 6.7 g/l and butyrate 0.8 g/L (no ethanol or butanol was present). Samples of the fermentation broth were taken at 24 h (see Table 13).

TABLE 13

Conversion of acids to alcohols under different CO partial pressures by *Clostridium autoethanogenum*, in the presence and absence of hydrogen.

| Gas composition | Acetate conc (g/L) | Ethanol conc (g/L) | Butyrate conc (g/L) | Butanol conc (g/L) |
|---|---|---|---|---|
| 100% CO (40 psia) | 4.7 | 1.8 | 0.4 | 0.3 |
| 100% CO (50 psia) | 4.2 | 1.9 | 0.3 | 0.4 |
| 75% CO 25% H2 (40 psia) | 5.5 | 1.3 | 0.5 | 0.2 |
| 60% CO 40% H2 (50 psia) | 5.0 | 1.6 | 0.5 | 0.5 |

Acids, such as butyric and acetic acids, can be converted to alcohols including ethanol and butanol in the presence of mixed CO/H2 substrates. Clearly, in the absence of H2, increased CO partial pressure improves overall conversion. However, the presence of H2, particular at elevated partial pressure also improves overall conversion.

Example 4C

Effect of Gas Composition on Ethanol Production

Serum vials were prepared in accordance with the above. Each serum vial was pressurised to 35 psig (50 psia) with the indicated gas and incubated at 37° C. with constant shaking. Samples of the fermentation broth were taken at 18 h (see Table 14).

TABLE 14

Conversion of acetate into ethanol under different CO partial pressures by *Clostridium autoethanogenum*, in the presence and absence of hydrogen.

| Gas composition | Change in acetate conc (g/L) | Change in alcohol conc (g/L) | End gas pressure (psia) | | |
|---|---|---|---|---|---|
| | | | CO | H2 | CO2 |
| 100% CO | −1.6 | +2.3 | 37 | — | 9 |
| 40% CO; 40% H2; 20% N2 | −1.2 | +2.5 | 0 | 8 | 11 |

Mixed substrates comprising CO and H2 can be used to convert acids to alcohols in the presence of C. auto. Interestingly, over the time scale of the experiment, significantly more alcohol is produced than acetate is consumed. This indicates that while acetate may be stoichiometrically converted into ethanol, additional acetate accumulates and may be converted to alcohol until CO is completely consumed.

Example 4E

Effect of CO and H2 Partial Pressure on Alcohol Production

Serum vials were prepared in accordance with the above. Each serum vial was pressurised to 35 psig (50 psia) with the indicated gas and incubated at 37° C. with constant shaking. Samples of the fermentation broth were taken at intervals of 1.5 h, 3 h, 5 h and 24 h (see table 15).

TABLE 15

Conversion of acetate into ethanol under different CO and H2 partial pressures by *Clostridium autoethanogenum*

| Gas composition | Time | Acetate conc (g/L) | Ethanol conc (g/L) | Pressure (psig) |
|---|---|---|---|---|
| 80% CO; 20% H2 | 0 | 10.8 | 0.2 | 35 |
| | 1.5 | 9.5 | 1.6 | 34.8 |
| | 3.25 | 9.3 | 2.4 | 32.2 |
| | 4.75 | 9.2 | 2.6 | 30.3 |
| | 6.75 | 9.4 | 2.5 | 28.7 |
| | 23 | 13.7 | 0.8 | 21.6 |
| 60% CO; 40% H2 | 0 | 10.8 | 0.2 | 35 |
| | 1.5 | 9.5 | 1.7 | 34.1 |
| | 3.25 | 9.5 | 2.6 | 30.6 |
| | 4.75 | 9.4 | 3.0 | 28.2 |
| | 6.75 | 9.5 | 3.1 | 25.4 |
| | 23 | 10.2 | 3.9 | 12.6 |

The results indicate that at elevated H2 levels, there is an improvement in overall conversion of acids into alcohols. However, it is considered that ethanol is reconverted back to acetate as H2 levels deplete over the course of the experiment, particularly at low levels of H2 (e.g. 20%).

Example 4F

Effect of CO Partial Pressure in Steel Mill Waste Gas

Serum vials were prepared in accordance with the above. Each serum vial was pressurised to 25 psig (40 psia) with steel mill waste gas (approx 53% CO; 18% CO2; 26% N2; 3% H2) and incubated at 37° C. with constant shaking. Samples of the fermentation broth were taken at intervals of 1 h, 3 h and 5 h (see Table 16).

TABLE 16

Conversion of acetate to ethanol at different CO partial pressures using steel mill waste gas.

| Initial Gas Pressure | Time | Acetate conc (g/L) | Ethanol conc (g/L) | Pressure (psig) | |
|---|---|---|---|---|---|
| 46 psia | 0 | 14.217 | 0.224 | 31 | 13.053 |
| | 1 | 13.335 | 0.696 | 31.2 | |
| | 3 | 12.775 | 1.811 | 26.4 | |
| | 5 | 13.053 | 2.197 | 21.2 | |
| 40 psia | 0 | 14.217 | 0.224 | 25 | |
| | 1 | 13.395 | 0.665 | 26.1 | |
| | 3 | 12.896 | 1.77 | 21.2 | |
| | 5 | 14.012 | 1.675 | 15.6 | |
| 30 psia | 0 | 14.217 | 0.224 | 15 | |
| | 1 | 13.485 | 0.623 | 15.9 | |
| | 3 | 12.909 | 1.742 | 11.9 | |
| | 5 | 14.363 | 1.364 | 8.2 | |

Steel mill waste gases can be used to convert acids into alcohols. Increasing CO partial pressure in the waste gas, has a beneficial effect on acid conversion.

Example 4G

Effect of CO2 Partial Pressure on Ethanol Production

Serum vials were prepared in accordance with the above. Each serum vial was pressurised to 35 psig (50 psia) with the indicated gas and incubated at 37° C. with constant shaking. Samples of the fermentation broth were taken at intervals of 1 h, 3 h and 5 h (see Table 17).

TABLE 17

Conversion of acetate to ethanol at different CO2 partial pressures by *Clostridium autoethanogenum*.

| Gas composition | Time | Acetate conc (g/L) | Ethanol conc (g/L) | Pressure (psig) |
|---|---|---|---|---|
| 40% CO; 60% N2 | 0 | 9.256 | 0 | 35 |
| | 1 | 8.798 | 0.502 | 35.3 |
| | 3 | 8.31 | 1.076 | 33.3 |
| | 5 | 7.89 | 1.478 | 30.9 |
| 40% CO; 50% N2; 10% CO2 | 0 | 9.256 | 0 | 35 |
| | 1 | 8.721 | 0.509 | 35 |
| | 3 | 8.078 | 1.092 | 33.4 |
| | 5 | 7.69 | 1.511 | 31.1 |
| 40% CO; 40% N2; 20% CO2 | 0 | 9.256 | 0 | 35 |
| | 1 | 8.778 | 0.488 | 35.4 |
| | 3 | 8.115 | 1.057 | 32.9 |
| | 5 | 7.383 | 1.461 | 31.2 |
| 40% CO; 30% N2; 30% CO2 | 0 | 9.256 | 0 | 35 |
| | 1 | 8.763 | 0.473 | 34 |
| | 3 | 8.12 | 0.994 | 32.8 |
| | 5 | 7.769 | 1.4 | 31 |
| 40% CO; 20% N2; 40% CO2 | 0 | 9.256 | 0 | 35 |
| | 1 | 8.761 | 0.465 | 34 |
| | 3 | 8.191 | 0.962 | 32.9 |
| | 5 | 7.771 | 1.366 | 30.6 |
| 40% CO; 10% N2; 50% CO2 | 0 | 9.256 | 0 | 35 |
| | 1 | 9.255 | 0 | 34.5 |
| | 3 | 9.527 | 0.106 | 34 |
| | 5 | 9.131 | 0.235 | 33 |
| 40% CO; 60% CO2 | 0 | 9.256 | 0 | 35 |
| | 1 | 8.814 | 0.384 | 32.2 |
| | 3 | 8.23 | 0.737 | 31.5 |
| | 5 | 8.365 | 1.046 | 30 |

Substrates comprising CO containing a variety of constituents can be sued to convert acids into alcohols. However, it is noted that increased levels of CO2 have a slight inhibitory effect on alcohol production.

Example 5

Effect of Formate Addition

Example 5A

Formate Concentration in Batch Vessels

Serum vials were prepared in accordance with the above. However, an aqueous formate solution was added to the empty vial and the pH adjusted to 5.5 with NaOH prior to inoculation. Each serum vial was pressurised to 25 psig with 50% CO; 12.5% CO2; 37.5% N2 gas and incubated at 37° C. with constant shaking. Samples of the fermentation broth were taken at 72 h (see Table 18).

TABLE 18

Conversion of acetate to ethanol in presence of formate at different concentrations using *Clostridium autoethanogenum*.

| Formate concentration (g/L) | Time (h) | Acetate conc (g/L) | Ethanol conc (g/L) | Pressure (psig) |
|---|---|---|---|---|
| 0 g/L | 0 | 11.10 | 0 | 25 |
|  | 1 | 11.36 | 0 | 25 |
|  | 4 | 10.98 | 0.25 | 22.9 |
|  | 20 | 13.38 | 0.158 | 13.3 |
|  | 48 | 13.00 | 0.16 | 13 |
|  | 72 | 13.70 | 0.17 | 12.7 |
| 2 g/L | 0 | 9.6 | 0 | 25 |
|  | 1 | 8.7 | 1.02 | 25 |
|  | 4 | 7.3 | 2.22 | 22.9 |
|  | 20 | 6.4 | 3.12 | 20.1 |
|  | 48 | 6.1 | 3.99 | 19.9 |
|  | 72 | 5.9 | 4.28 | 18.1 |
| 5 g/L | 0 | 9.6 | 0 | 25 |
|  | 1 | 8.7 | 0.85 | 25 |
|  | 4 | 7.3 | 1.92 | 22.9 |
|  | 20 | 6.4 | 2.65 | 20.7 |
|  | 48 | 6.1 | 3.44 | 19.9 |
|  | 72 | 5.9 | 3.76 | 19.1 |

In the absence of formate, C. auto continues to produce acetate and a small amount of alcohol. However, when formate is added to the fermentation reaction, acetate is converted to alcohol in substantially stoichiometric quantities. The conversion rate is highest at low concentrations of formate (2 g/L), indicating there may be an inhibitory and/or toxic effect at higher formate concentrations.

Example 5B

Formate Addition in a CSTR

5 L of anaerobic fermentation media (prepared as described above) in a 5 Liter CSTR was inoculated with an actively growing *Clostridium autoethanogenum* culture (DSMZ 19630) at a level of 5% (v/v). A continuous flow of 70% CO and 15% $CO_2$ 1% $H_2$ 14% $N_2$ gas was introduced at the bottom of the fermenter vessel through a diffusing sparger at a volumetric flow rate of 60 ml/minutes. The initial pH of the fermenter was maintained at 5.5. Following several days of microbial growth, a continuous culture was established by switching on a pump introducing fresh fermentation media sparged with $N_2$ into the CSTR at a flow rate of 2 mL/min. Level controllers are employed to maintain the correct level of culture within the fermenter vessel, set by using a level probe and pump which automatically switches on when level in fermenter vessels rises too high and pumps culture out of the vessel until level drops back down to set level, this allows for a steady supply of fresh media to be provided to the culture and an actively growing, high viability culture to be maintained.

After several days of continuous operation, the supply of fresh media was stopped and the fermenter returned to a batch configuration. At time=0 (FIG. 2) formic acid (15 mL) was added and the pH adjusted to 5.5 by adding NaOH. Over the course of approximately 30 minutes, pH of the fermentation media rose to 6 as acetate was consumed by the culture and ethanol was produced. Consequently, additional formic acid (3 mL) was added to lower pH back down to 5.5. At approximately t=60 min, formic acid was introduced via a dosing pump configured to automatically dose into the reactor when the pH rose above the set point of 5.5. The formate dosing pump was run for approximately 5 hours, over which time acetate was consumed by the culture and ethanol was produced.

The results show a fermentation reaction continuously producing acetate can be switched from acetate production to conversion of acetate to alcohol by perturbing the system, e.g. by adding formate. The conversion is substantially stoichiometric over the course of the experiment.

Example 6

Effect of Additional Acetate Addition

1 L anaerobic fermentation media (prepared as described above with the following alterations: a lower concentration vitamin solution [0.4 ml/L LS03 without pantothenic acid and 500 ul/L of pantothenic acid solution (40 mg/L)] was added to the stock solution) in a 1 L CSTR was inoculated with an actively growing *Clostridium autoethanogenum* culture (DSMZ 19630) at a level of 5% (v/v). A continuous flow of 35% CO and 60% $H_2$ 5% CH4 gas was introduced at the bottom of the fermenter vessel through a diffusing sparger at a volumetric flow rate of 10 ml/minute. The initial pH of the fermenter was maintained at 5.5. Following several days of microbial growth, the gas flow rate increased to 20 ml/minute and the agitation increased from 200 rpm to 500 rpm. A continuous culture was established by introducing fresh media (prepared as described above with the following alterations: a lower concentration vitamin solution [0.4 ml/L LS03 without pantothenic acid and 1 ml/L of pantothenic acid solution (40 mg/L)] was added to the stock solution) while maintaining a constant media volume in the fermenter. The fresh media flow rate was increased from 6 ml/hour to 54 ml/hour over several weeks. After several weeks continuous operation, the gas supply was changed to 35% CO 45% $H_2$ 15% CH4 5% CO2 and operated for several weeks. Ethanol productivity was maintained at approximately 6 g/L/day. On day 52, the fresh media supplied to the continuous culture was supplemented with 15 g/L acetic acid buffered to pH 5.5 for 2 days. During this time, alcohol productivity increased to approximately 15 g/L (day 53—FIG. 3) then 12 g/L (day 54). It is considered that a large portion of the acetate introduced into the fermenter was converted to alcohol.

The results show that alcohol productivity can be improved in a fermentation reaction continuously producing alcohol(s) by adding additional acid(s). Adding additional acid(s) (e.g. acetate) perturbs the fermentation reaction such that a substantial portion of the added acid(s) is converted to alcohol(s), such as ethanol.

Example 7

Effect of pH on Ethanol Production Using CO Containing Gas

1 L media of anaerobic LM33 fermentation media in a 1 Liter CSTR was inoculated with an actively growing *Clostridium autoethanogenum* culture (DSMZ 19630) at a level of 5% (v/v). A continuous flow of 70% CO and 15% $CO_2$ 1% $H_2$ 14% $N_2$ gas was introduced at the bottom of the fermenter vessel through a diffusing sparger at a volumetric flow rate of 19 ml/minutes. The initial pH of the fermenter was set to 5.5. For the majority of the experiment, the acetic acid concentration of the culture was maintained below 4 g/L by a cell recycle and media exchange system. The cells were passed through a cross flow membrane Viva 200, the filtrate was collected and the cells were returned to the reactor vessel. The filtrate was replaced with fresh media to ensure the medium volume inside the reactor remained constant. On day 3 the cell recycling system was switched off and the pH, which had been maintained at approximately 5.6 for 3 days, with ORP fluctuating between −400 and −430 mV was increased. The pH was adjusted to approximately 5.9, and the ORP decreased to approximately −470 mV.

These results show that, at pH 5.6, acetate and ethanol are produced simultaneously, with an excess of acetate. Referring to FIG. 4, this stage of the fermentation is also associated with a period of microbial growth. When the pH is increased the ORP decreased to approximately −470 mV and the rate of alcohol production increased to approximately 1.2 g/L/day, while some acetate was consumed at a rate of approximately 0.2 g/L/day. Accordingly, the microbial culture can be switched from a production phase where acetate is produced, to a conversion phase where acetate is converted to ethanol by adjusting pH of the liquid nutrient medium.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method for converting acid(s) to corresponding alcohol(s) using a microbial culture in the presence of a substrate comprising CO or CO and $H_2$, said method comprising:
   (a) culturing, in a bioreactor, one or more strains of carboxydotrophic bacteria in the presence of said substrate to produce one or more acids and optionally one or more alcohols; and
   (b) perturbing the microbial culture, such that at least a portion of the microbial culture is switched from a substantially production phase to a substantially conversion phase, whereby at least a portion of at least one of the one or more of said acids is converted to its corresponding alcohol; and
   (c) recovering at least a portion of the alcohol(s).

2. The method of claim 1, wherein the concentration of $H_2$ in the substrate is less than 40% by volume.

3. The method of claim 2, wherein the concentration of $H_2$ in the substrate is less than 5% by volume.

4. The method of claim 1, wherein the bacteria are selected from the group consisting of *Clostridium, Moorella, Pyrococcus, Eubacterium, Desulfobacterium, Carboxydothermus, Acetogenium, Acetobacterium, Acetoanaerobium, Butyribacterium* and *Peptostreptococcus*.

5. The method of claim 1, wherein the carboxydotrophic bacteria has all the defining features of *Clostridium autoethanogenum* strain deposited at the German Resource Centre for Biological Material (DSMZ) under the identifying deposit number DSMZ 10061.

6. The method of claim 1, wherein the one or more acids of step (a) are produced continuously, and, the one or more acids are continuously converted to the corresponding alcohol in step (b).

7. The method of claim 1, wherein said one or more alcohols are produced in step (a) and a substantially greater amount of acid is produced in step (a) relative to the quantity of alcohol produced in step (a).

8. The method of claim 1, wherein the acid produced in step (a) is acetate and the corresponding alcohol is ethanol.

9. The method of claim 1, further comprising adding an acid to the bioreactor during step (a) and/or step (b) and converting said added acid to its corresponding alcohol.

10. The method of claim 1, wherein the acid(s) in steps (a) or (b) are mono or di-carboxylic acids.

11. The method of claim 1, wherein the perturbing step is carried out by one or more of:
   i. adjusting the pH of a liquid nutrient medium containing the microbial culture;
   ii. adjusting the open redox potential of a liquid nutrient medium containing the microbial culture;
   iii. adding a second acid to the bioreactor;
   iv. adding one or more reducing agents to the bioreactor;
   v. adjusting the CO concentration in a liquid nutrient medium containing the microbial culture;
   vi. adjusting the CO partial pressure in the bioreactor.

12. The method of claim 1, further comprising carrying out step (a) in a first bioreactor and step (b) in a second bioreactor.

13. The method of claim 1, wherein the substrate comprising CO comprises at least 15% to about 100% CO by volume.

14. The method of claim 11, wherein the perturbing step comprises the addition of a second acid and the acid is selected from the group consisting of formate, acetate and mixtures thereof.

15. The method of claim 11, wherein the perturbing step comprises the addition of a reducing agent and the reducing agent is selected from the group consisting of sodium dithionite, cysteine sodium sulphide and mixtures thereof.

16. The method of claim 11, wherein the perturbing step comprises adjusting the CO concentration by increasing the CO concentration in the liquid nutrient medium by at least 1 mmol.

17. The method of claim 11, wherein the perturbing step comprises adjusting the CO partial pressure by increasing the partial pressure by at least 15 psi.

18. The method of claim 11, wherein the perturbing step comprises adjusting the CO partial pressure by increasing the partial pressure above a sufficient threshold pressure of at least 37 psia.

* * * * *